(12) United States Patent
Mizuguchi et al.

(10) Patent No.: US 10,889,805 B2
(45) Date of Patent: Jan. 12, 2021

(54) INTESTINAL EPITHELIOID CELLS

(71) Applicants: National Institutes of Biomedical Innovation, Health and Nutrition, Osaka (JP); Osaka University, Osaka (JP)

(72) Inventors: Hiroyuki Mizuguchi, Osaka (JP); Kazuo Takayama, Osaka (JP)

(73) Assignees: NATIONAL INSTITUTES OF BIOMEDICAL INNOVATION, HEALTH AND NUTRITION, Osaka (JP); OSAKA UNIVERSITY, Osaka (JP)

( * ) Notice: Subject to any disclaimer, the term of this patent is extended or adjusted under 35 U.S.C. 154(b) by 614 days.

(21) Appl. No.: 15/557,477

(22) PCT Filed: Mar. 9, 2016

(86) PCT No.: PCT/JP2016/057312
§ 371 (c)(1),
(2) Date: Sep. 12, 2017

(87) PCT Pub. No.: WO2016/147975
PCT Pub. Date: Sep. 22, 2016

(65) Prior Publication Data
US 2018/0320144 A1 Nov. 8, 2018

(30) Foreign Application Priority Data
Mar. 13, 2015 (JP) ................................. 2015-051475

(51) Int. Cl.
*C12N 5/00* (2006.01)
*C12N 1/00* (2006.01)
(Continued)

(52) U.S. Cl.
CPC .............. *C12N 5/10* (2013.01); *C12N 5/067* (2013.01); *C12N 5/0679* (2013.01); *C12Q 1/025* (2013.01);
(Continued)

(58) Field of Classification Search
None
See application file for complete search history.

(56) References Cited

U.S. PATENT DOCUMENTS

2012/0183989 A1 7/2012 Matsui et al.
2012/0231490 A1 9/2012 Mizuguchi et al.

FOREIGN PATENT DOCUMENTS

JP 2013252081 A 12/2013
WO 2009013254 A1 1/2009
(Continued)

OTHER PUBLICATIONS

Takayama et al. "Generation of metabolically functioning hepatocytes from human pluripotent stem cells by FOXA2 and HNF1α transduction", Journal of Hepatology, 2012, vol. 57, 628-636. (Year: 2012).*
(Continued)

*Primary Examiner* — Kevin K Hill
*Assistant Examiner* — James Joseph Graber
(74) *Attorney, Agent, or Firm* — Kilyk & Bowersox, P.L.L.C.

(57) ABSTRACT

Provided is a selective method for inducing differentiation from pluripotent stem cells to enterocyte-like cells. Also provided is an excellent enterocyte-like cell expressing drug-metabolizing enzymes and drug transporters. More specifically, provided is an enterocyte-like cell having properties closer to those of primary enterocytes, which are difficult to acquire. The foregoing is achieved by adding an ALK5 inhibitor (SB431542), Wnt3a, and EGF to a culture system of definitive endoderm cells obtained by differentia-
(Continued)

tion induction from pluripotent stem cells and extending a culture time. The foregoing is also achieved by introducing CDX2 gene and/or FOXA2 gene into the pluripotent stem cells or the definitive endoderm cells. The foregoing is also achieved by overlaying a basement membrane matrix on the enterocyte-like cells.

4 Claims, 21 Drawing Sheets

Specification includes a Sequence Listing.

(51) Int. Cl.
- C12N 5/10 (2006.01)
- G01N 33/50 (2006.01)
- C12N 5/071 (2010.01)
- C12Q 1/02 (2006.01)

(52) U.S. Cl.
CPC ...... *G01N 33/5073* (2013.01); *C12N 2501/11* (2013.01); *C12N 2501/115* (2013.01); *C12N 2501/12* (2013.01); *C12N 2501/15* (2013.01); *C12N 2501/155* (2013.01); *C12N 2501/16* (2013.01); *C12N 2501/237* (2013.01); *C12N 2501/415* (2013.01); *C12N 2502/14* (2013.01); *C12N 2506/02* (2013.01); *C12N 2506/45* (2013.01)

(56) References Cited

FOREIGN PATENT DOCUMENTS

| WO | 2011024592 A1 | | 3/2011 | |
|----|---------------|---|--------|---|
| WO | 2011052504 A1 | | 5/2011 | |
| WO | 2014132933 A1 | | 9/2014 | |
| WO | WO/2014/132933 | * | 9/2014 | ......... C12N 2501/11 |

OTHER PUBLICATIONS

Iwao et al. "Differentiation of Human Induced Pluripotent Stem Cells into Functional Enterocyte-like Cells Using a Simple Method", Drug Metab. Pharmacokinet. 29 (1): 44-51 (2014), Advanced Published Date: Jul. 2, 2013. (Year: 2013).*

Ogaki et al. "Wnt and Notch Signals Guide Embryonic Stem Cell Differentiation into the Intestinal Lineages" Stem Cells, 2013; 31:1086-1096. (Year: 2013).*

Suh et al. "An Intestine-Specific Homeobox Gene Regulates Proliferation and Differentiation", Molecular and Cellular Biology, Feb. 1996, vol. 16, No. 2, p. 619-625. (Year: 1996).*

Kauffman et al. "Alternative functional in vitro models of human intestinal epithelia", Front Pharmacol. 2013; vol. 4, Article 79, pp. 1-18. (Year: 2013).*

Hansen et al. "Cytochrome P450 enzyme activity and protein expression in primary porcine enterocyte and hepatocyte cultures", XENOBIOTICA, 2000, vol. 30, No. 1, 27-46. (Year: 2000).*

Chougule et al. "Isolation and characterization of human primary enterocytes from small intestine using a novel method", Scandinavian Journal of Gastroenterology. 2012; 47: 1334-1343. (Year: 2012).*

Tojo et al., "The ALK-5 inhibitor A-83-01 inhibits Smad signaling and epithelial-to-mesenchymal transition by transforming growth factor-β", Cancer Sci, Nov. 2005, vol. 96, No. 11, pp. 791-800. (Year: 2005).*

Green et al. "Generation of anterior foregut endoderm from human embryonic and induced pluripotent stem cells" Nature Biotechnology 2011, vol. 29 No. 3. (Year: 2011).*

Huang et al. "The in vitro generation of lung and airway progenitor cells from human pluripotent stem cells", Nature Protocols, vol. 10, No. 3 (Feb. 2015). (Year: 2015).*

International Search Report issued in corresponding International Patent Application No. PCT/JP2016/057312 dated Jun. 14, 2016 (2 pages).

Forster et al., "Human Intestinal Tissue with Adult Stem Cell Properties Derived from Pluripotent Stem Cells," Stem Cell Reports, vol. 2, No. 6, 2014, pp. 838-852.

Ogaki et al., "Wnt and Notch Signals Guide Embryonic Stem Cell Differentiation into the Intestinal Lineages," Stem Cells, vol. 31, No. 6, 2013, pp. 1086-1096.

Ozawa et al., "Preparation of intestinal epithelial cells derived from human ES / iPS cells for aiming the application to pharmacokinetic evaluation system," The 37th Annual Meeting of the Molecular Biology Society of Japan, Nov. 25, 2014, (3 pages).

Ozawa et al., "Generation of enterocyte-like cells from human induced pluripotent stem cells for drug absorption and metabolism studies in human small intestine," Scientific Reports, vol. 5, No. 16479, DOI: 10.1038/srep16479, 2015, pp. 1-11 (22 pages).

Spence et al., "Directed differentiation of human pluripotent stem cells into intestinal tissue in vitro," Nature, doi: 10.1038/nature09691, vol. 470, 2011, pp. 105-109 (9 pages).

* cited by examiner

FIG. 1A  DIFFERENTIATION INDUCTION PROTOCOL
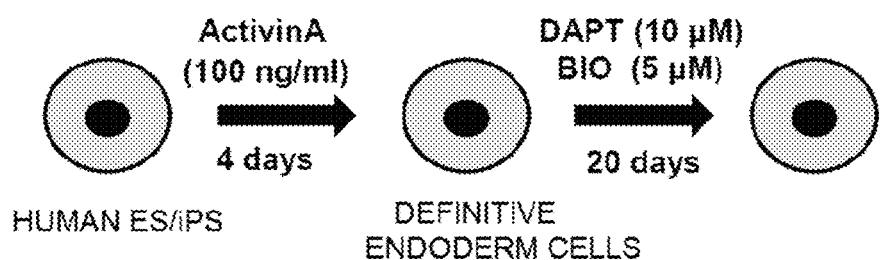
FIG. 1B  DIFFERENTIATION INDUCTION EFFICIENCY
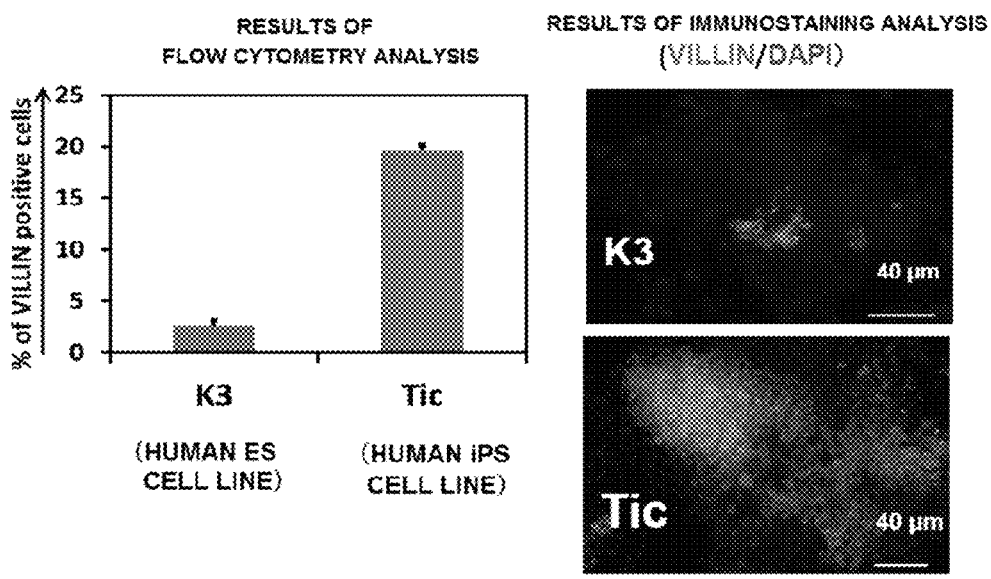

FIG. 2A  DIFFERENTIATION INDUCTION PROTOCOL
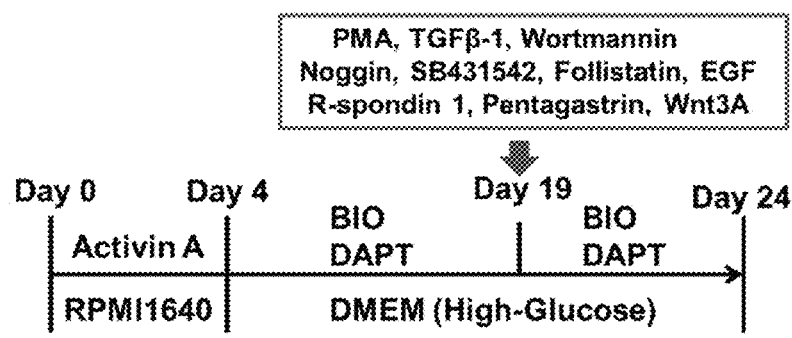
FIG. 2B
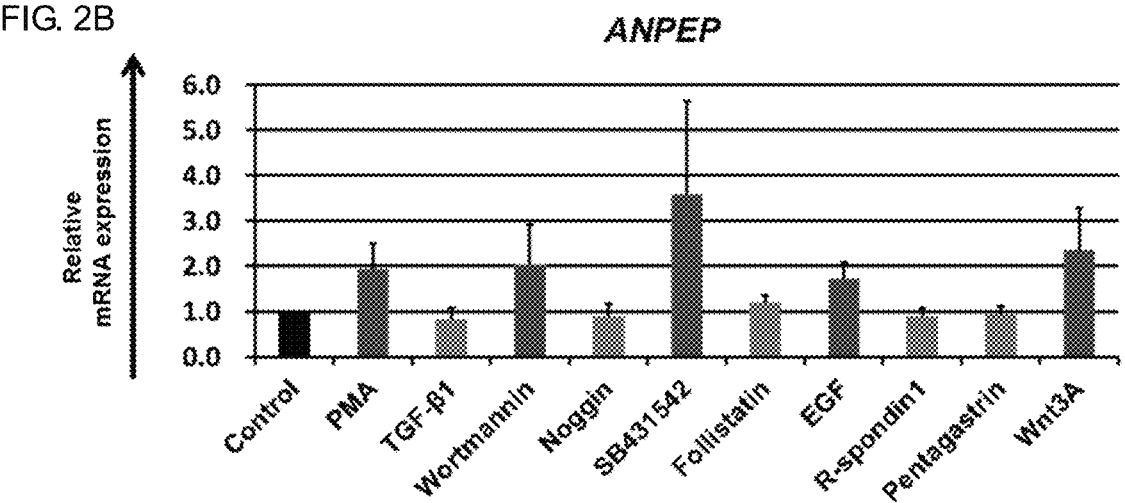

FIG. 3A    DIFFERENTIATION INDUCTION PROTOCOL
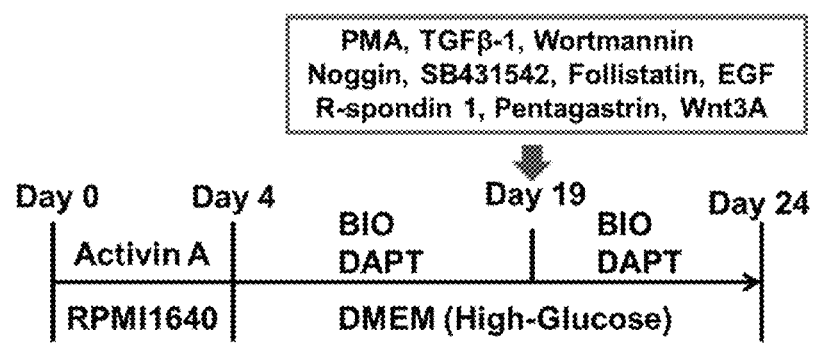
FIG. 3B    ENTEROCYTE MARKER *VILLIN*
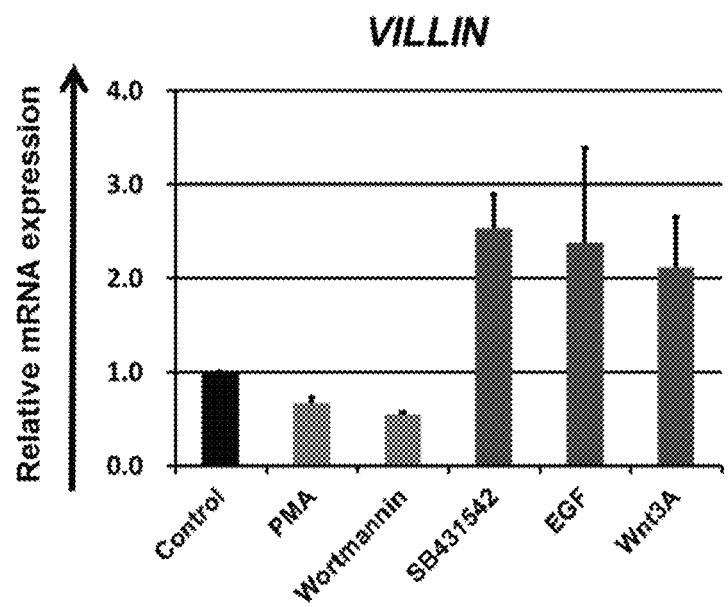

FIG. 4A  DIFFERENTIATION INDUCTION PROTOCOL
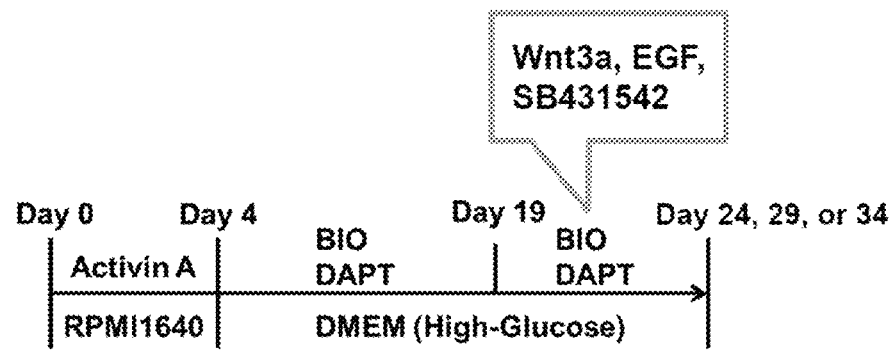
FIG. 4B  ENTEROCYTE MARKER *ANPEP*
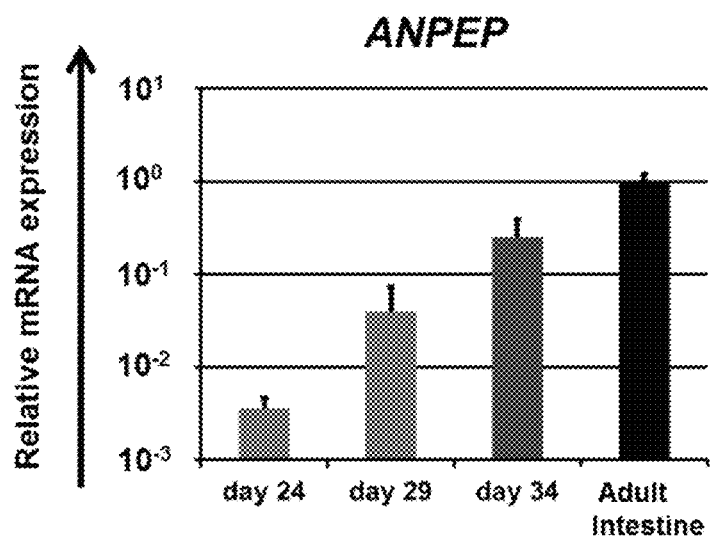

FIG. 5A  DIFFERENTIATION INDUCTION PROTOCOL
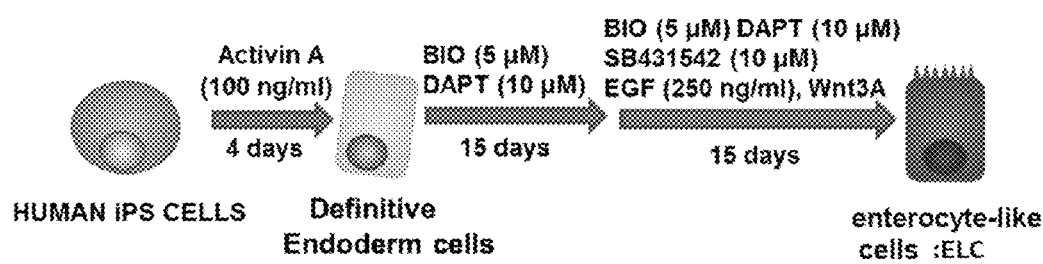
FIG. 5B  VILLIN POSITIVE RATE
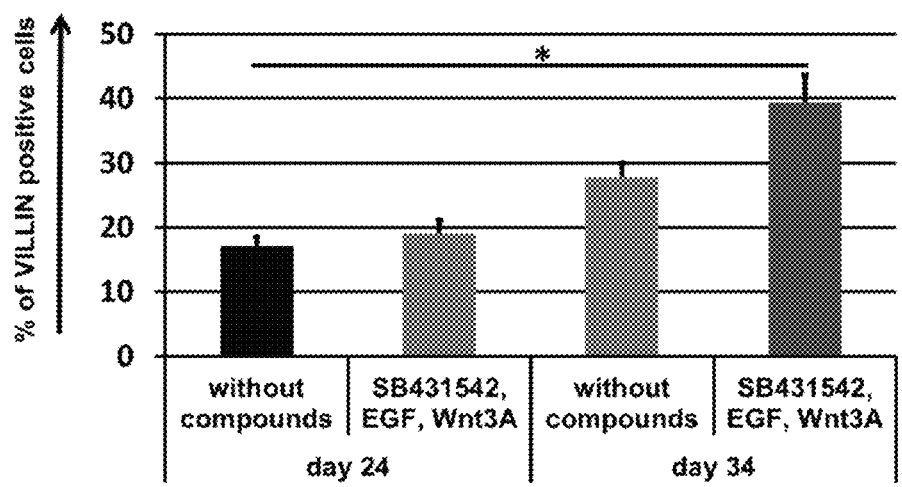

FIG. 6A  DIFFERENTIATION INDUCTION PROTOCOL
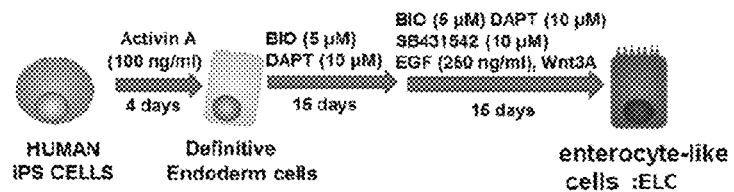
FIG. 6B  ANALYSIS OF GENE EXPRESSION OF TRANSPORTER PEPT1
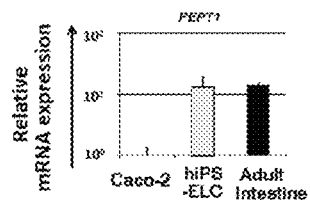
FIG. 6C  ANALYSIS OF GENE EXPRESSION OF BASOLATERAL TRANSPORTERS
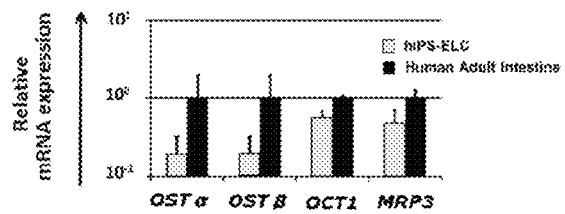
FIG. 6D  ANALYSIS OF GENE EXPRESSION OF APICAL TRANSPORTERS
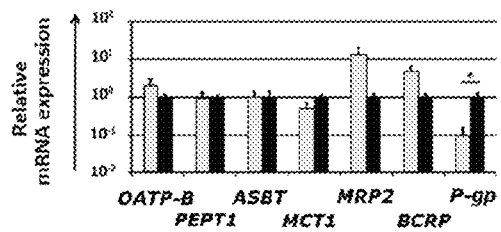

FIG. 7A  DIFFERENTIATION INDUCTION PROTOCOL
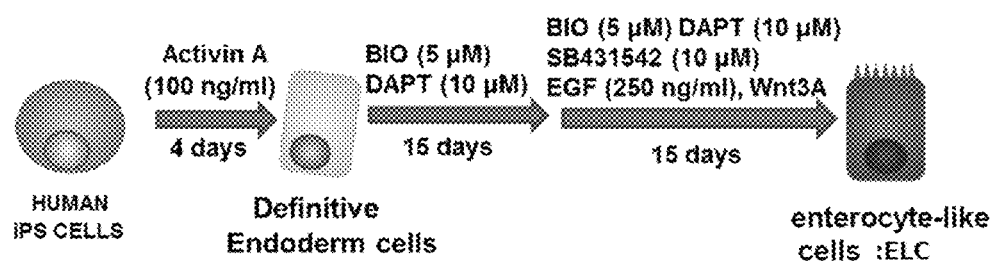
FIG. 7B  TIGHT JUNCTION FORMATION
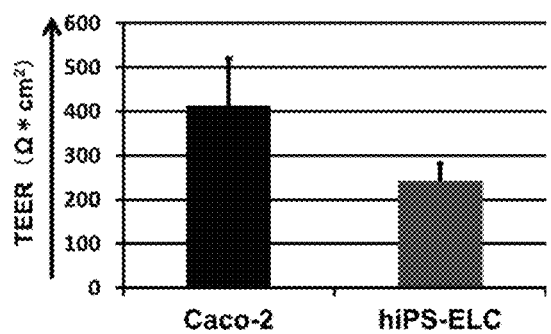
FIG. 7C  ZO-1 EXPRESSION
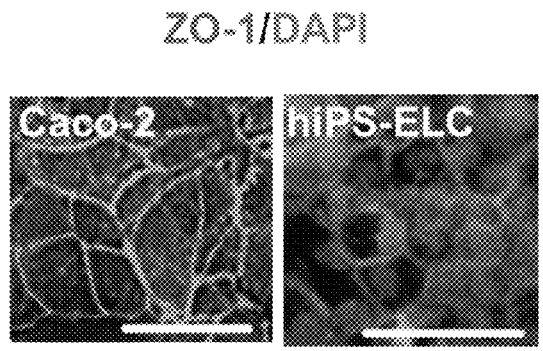

FIG. 8A  DIFFERENTIATION INDUCTION PROTOCOL
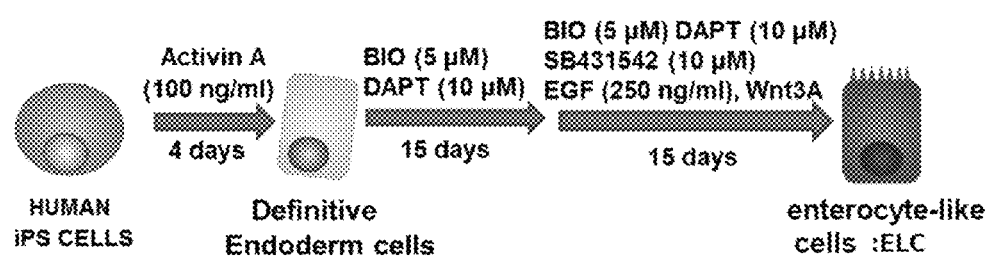
FIG. 8B  ANALYSIS OF GENE EXPRESSION OF DRUG-METABOLIZING ENZYME CYP3A4
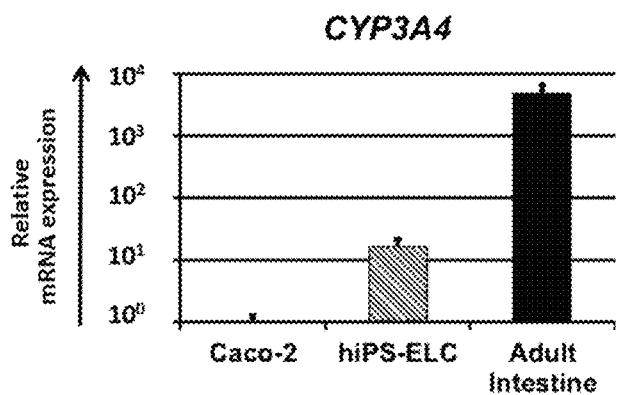

FIG. 9A   DIFFERENTIATION INDUCTION PROTOCOL
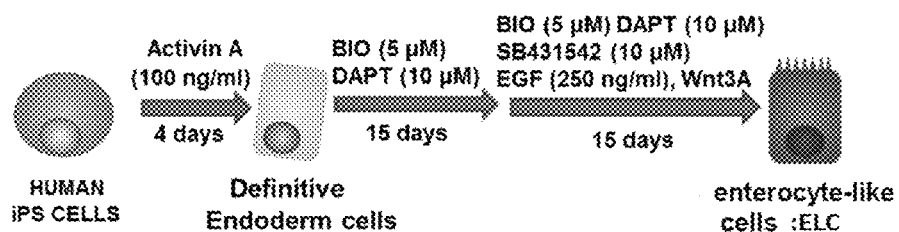
FIG. 9B   CYP3A4 INDUCTION TEST WITH VITAMIN D3
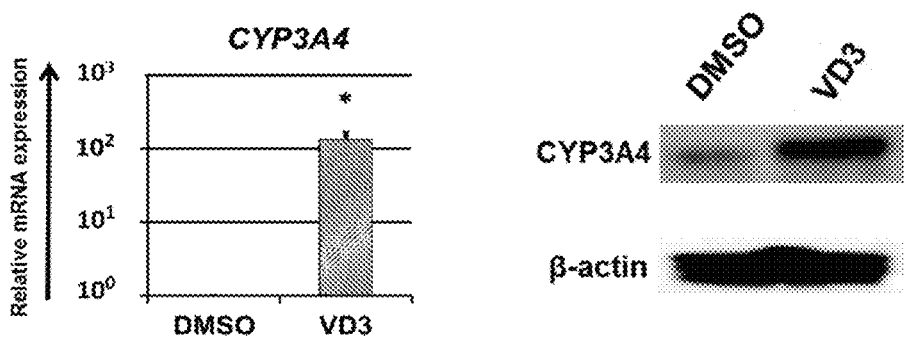
FIG. 9C   CYP3A4 INDUCTION TEST WITH RIFAMPICIN
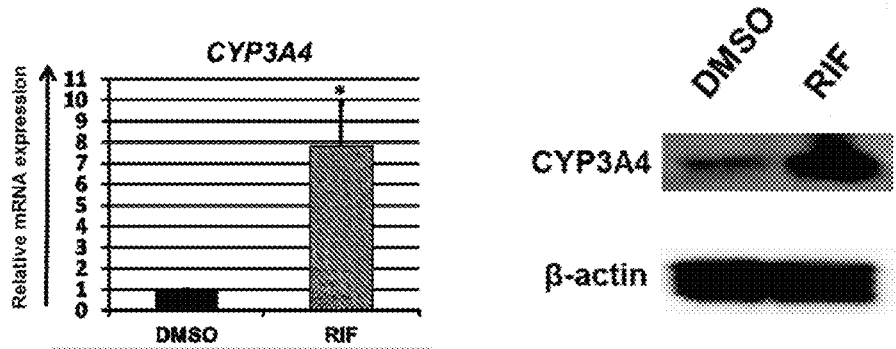

FIG. 10A  DIFFERENTIATION INDUCTION PROTOCOL
USING GENE TRANSFER METHOD
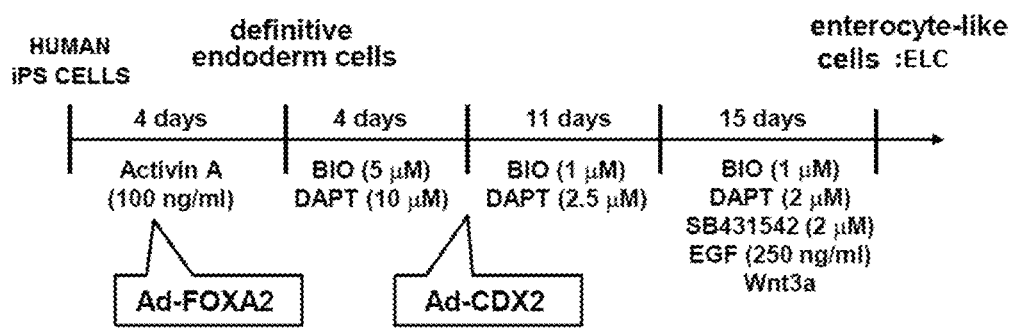
FIG. 10B  ANALYSIS OF SMALL INTESTINE-RELATED GENE EXPRESSION
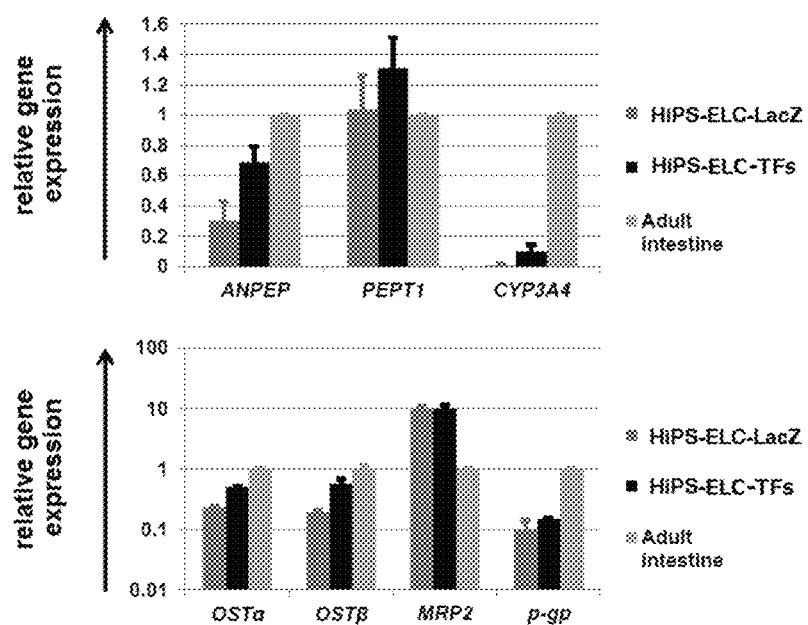

FIG. 11A  DIFFERENTIATION INDUCTION PROTOCOL USING GENE TRANSFER METHOD
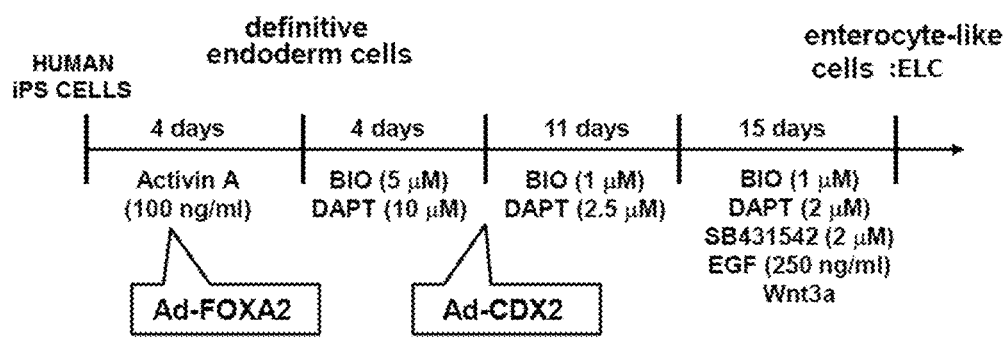
FIG. 11B  VILLIN POSITIVE RATE
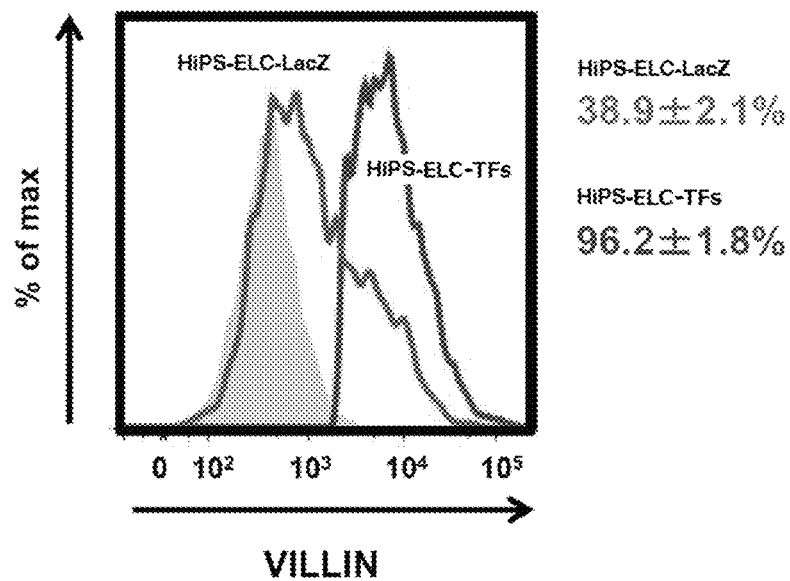

FIG. 12A  DIFFERENTIATION INDUCTION PROTOCOL USING GENE TRANSFER METHOD
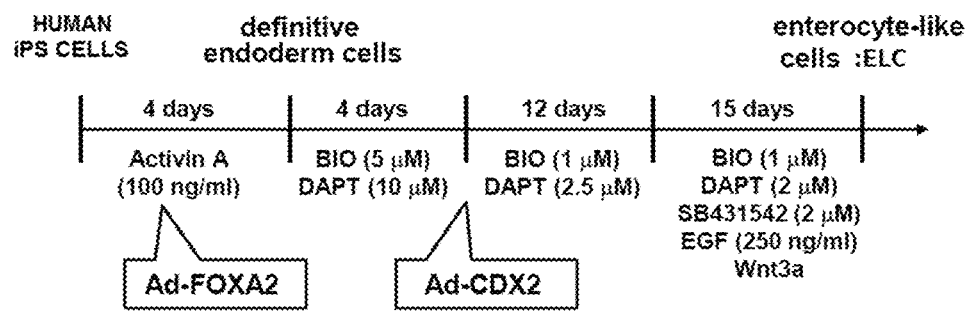
FIG. 12B  CYP3A4/P-gp INDUCTION TEST WITH VITAMIN D3
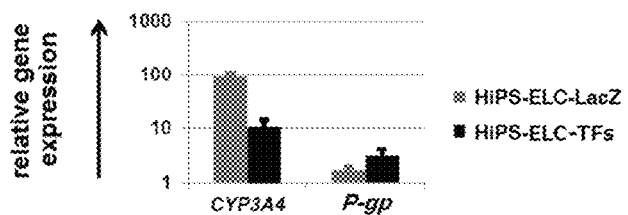
FIG. 12C  CYP3A4/P-gp INDUCTION TEST WITH RIFAMPICIN
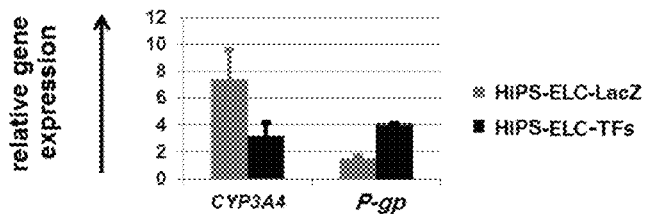

DIFFERENTIATION INDUCTION PROTOCOL

INTESTINAL EPITHELIOID CELLS

TECHNICAL FIELD

The present invention relates to a method for inducing differentiation from pluripotent stem cells to enterocyte-like cells, and also relates to an enterocyte-like cell obtained by the method for inducing differentiation. More specifically, the present invention relates to an excellent enterocyte-like cell expressing a drug-metabolizing enzyme and a drug transporter and having a tight junction function.

The present application is a National Stage Application of PCT/JP2016/057312, filed Mar. 9, 2016, which claims priority from Japanese Patent Application No. 2015-51475, which are incorporated herein by reference.

BACKGROUND ART

Pluripotent stem cells are undifferentiated cells having pluripotency and a self-replication ability, and cells obtained by differentiation induction from the pluripotent stem cells are suggested to have a tissue restoration ability after tissue damage. Thus, the pluripotent stem cells and their differentiated cells have been intensively investigated because the cells are useful in the fields of screening substances for treating various diseases and of regenerative medical treatments. Among the pluripotent stem cells, iPS cells are induced pluripotent stem cells that are generated by dedifferentiating somatic cells. Specifically, the iPS cells are generated by introducing genes encoding specific transcription factors, for example, OCT3/4, SOX2, KLF4, C-MYC, and the like into somatic cells, such as fibroblasts. In theory, cells having pluripotency can be induced to differentiate into all tissues and organs including enterocytes and the like.

Non Patent Literature 1 (Nature, 2011 Feb. 3, 470(7332): 105-9) is a paper on the world's first generation of a small intestinal tissue from human pluripotent stem cells. In the paper, it is disclosed that organoids containing all of enterocytes, Paneth cells, goblet cells, and enteroendocrine cells present in a small intestine can be generated. Non Patent Literature 2 (Stem Cell Reports, 2014 Jun. 3, 2(6): 838-52) is a paper reporting that small intestinal stem cells capable of long-term self-renewal can be generated from human pluripotent stem cells. The small intestinal stem cells generated in the paper can differentiate into organoids containing all of enterocytes, Paneth cells, goblet cells, and enteroendocrine cells present in the small intestine like those of Non Patent Literature 1.

Non Patent Literature 3 (Stem Cells, 2013 Jun. 31(6): 1086-96) is a paper reporting that induction of differentiation from mouse or human pluripotent stem cells to cells of small intestinal lineages can be promoted by using, for example, 6-bromoindirubin-3'-oxime (BIO), which is GSK-3 Inhibitor IX, and N-[(3,5-difluorophenyl)acetyl]-L-alanyl-2-phenyl]glycine-1,1-dimethylethyl ester (DAPT), which is a γ-secretase inhibitor. The combined use of BIO and DAPT enables induction of efficient differentiation from pluripotent stem cells to CDX2-positive cells. CDX2 is a master transcription factor controlling intestinal differentiation, expressed in all of a hindgut, small intestinal stem cells, small intestinal progenitor cells, and enterocytes.

Non Patent Literature 4 (Drug Metab Pharmacokinet, 2014; 29(1): 44-51) is a paper in which differentiation from human pluripotent stem cells to enterocyte-like cells is attempted. As a result, enterocyte-like cells expressing small intestinal markers, such as sucrase isomaltase (SI), solute carrier family 15 member 1 (SLC15A1)/peptide transporter 1 (PEPT1), and leucine-rich repeat containing G protein-coupled receptor 5 (LGR5), can be generated. In addition, the generated enterocyte-like cells are capable of uptake of a dipeptide β-Ala-Lys-N-7-amino-4-methylcoumarin-3-acetic acid (β-Ala-Lys-AMCA). However, the generated enterocyte-like cells have a problem in that expression of a drug-metabolizing enzyme CYP3A4 (Cytochrome P450 3A4) is extremely low (about 1/500) as compared to that in the human small intestine.

There is a disclosure of a gene transfer method in the case of effective differentiation induction from stem cells, such as ES cells or iPS cells, to hepatocytes using a vector system for next-generation gene therapy (Patent Literature 1: WO 2011/052504 A1). In Patent Literature 1, there is a disclosure that stem cells, such as ES cells or iPS cells, can be effectively induced to differentiate into hepatocytes by introducing, for example, any one or more kinds of genes selected from HEX gene, HNF4α gene, HNF6 gene, and SOX17 gene into the stem cells by using an adenovirus vector (hereinafter referred to as "Ad vector").

As shown by Non Patent Literatures 1 to 4 above, there are reports in which differentiation to enterocytes is attempted. However, there is still no report that enterocytes that enable simultaneous evaluation of drug metabolism and drug absorption have been able to be efficiently generated from human pluripotent stem cells. In addition, as shown by Patent Literature 1, there is a report in which differentiation from stem cells, such as ES cells or iPS cells, to hepatocytes is effectively induced using a vector system for next-generation gene therapy. However, there is no report in which differentiation to enterocytes is attempted using such vector system.

CITATION LIST

Non Patent Literature

[NPL 1] Nature, 2011 Feb. 3; 470(7332): 105-9
[NPL 2] Stem Cell Reports, 2014 Jun. 3; 2(6): 838-52
[NPL 3] Stem Cells, 2013 Jun. 31(6): 1086-96
[NPL 4] Drug Metab Pharmacokinet, 2014; 29(1): 44-51

Patent Literature

[PTL 1] WO 2011/052504 A1

SUMMARY OF INVENTION

Technical Problem

Hitherto, it has been difficult to acquire human primary enterocytes, and the obtained cells have had a problem of differences in properties due to individual differences. At present, Caco-2 cells (human colon carcinoma-derived cell line) are used as in vitro absorption evaluation system model cells for a small intestine. The Caco-2 cells can form strong tight junctions, and hence are used as a model for predicting drug permeation in the small intestine. However, unlike human enterocytes, the Caco-2 cells hardly express a drug-metabolizing enzyme CYP3A4, and hence do not enable the evaluation of a drug metabolism capacity. In addition, the Caco-2 cells are derived from cancer cells, and hence can hardly be said to reflect drug metabolism and permeability of normal human enterocytes. For those reasons, there have not existed excellent cells that enable stable testing for drug metabolism and permeability in the small intestine.

An object of the present invention is to provide a selective method for inducing differentiation from pluripotent stem cells to enterocyte-like cells, and another object of the present invention is to provide an excellent enterocyte-like cell expressing drug-metabolizing enzymes and drug transporters. A more specific object of the present invention is to provide an enterocyte-like cell having properties closer to those of human primary enterocytes, which are difficult to acquire.

Solution to Problem

The inventors of the present invention have conducted further investigations on a culture medium and a culture time on the basis of related-art methods of generating enterocyte-like cells in order to achieve the above-mentioned objects. As a result, the inventors have found that differentiation from pluripotent stem cells to enterocyte-like cells can be effectively induced by adding an ALK5 inhibitor (SB431542), Wnt3a, and epidermal growth factor (EGF) to a culture system and extending the culture time, and thus have completed the present invention. In addition, the inventors have found that differentiation from pluripotent stem cells to enterocyte-like cells can be effectively induced also by introducing CDX2 gene and/or FOXA2 gene, and thus have completed the present invention. Further, the inventors have found that differentiation from pluripotent stem cells to enterocyte-like cells can be induced also by overlaying a basement membrane matrix on cells during differentiation induction, and thus have completed the present invention.

That is, the present invention includes the following.
1. A method for inducing differentiation from pluripotent stem cells to enterocyte-like cells, the method including the steps of:
   1) inducing differentiation from pluripotent stem cells to definitive endoderm cells; and
   2) culturing the definitive endoderm cells obtained by the inducing differentiation in a system containing any one or more kinds of substances selected from an ALK5 inhibitor, Wnt3a, and EGF.
2. A method for inducing differentiation from pluripotent stem cells to enterocyte-like cells according to Item 1, further including a step of introducing CDX2 gene during any one of the step 1) or the step 2).
3. A method for inducing differentiation from pluripotent stem cells to enterocyte-like cells according to Item 1 or 2, further including a step of introducing FOXA2 gene during any one of the step 1) or the step 2).
4. A method for inducing differentiation according to any one of Items 1 to 3, in which the step 2) includes culturing the definitive endoderm cells obtained by the inducing differentiation in a system containing BIO and/or DAPT.
5. A method for inducing differentiation according to Item 4, further including, after the step of culturing the definitive endoderm cells in a system containing BIO and/or DAPT in the step 2), a treatment step of overlaying a basement membrane matrix on the cultured cells.
6. An enterocyte-like cell, which is obtained by the method for inducing differentiation of any one of Items 1 to 5.
7. An enterocyte-like cell, which is obtained from a pluripotent stem cell by artificially performing differentiation induction treatment, the enterocyte-like cell expressing drug-metabolizing enzymes and/or drug transporters.
8. A culture product, which is obtained through treatment by the method for inducing differentiation of any one of Items 1 to 5 and culture.
9. A evaluation method for drug-induced toxicity and/or a evaluation method for pharmacokinetics, including using the enterocyte-like cell of Item 6 or 7.
10. A method for drug-drug interaction test, including using the enterocyte-like cell of Item 6 or 7.
11. A CYP induction assay, including using the enterocyte-like cell of Item 6 or 7.

Advantageous Effects of Invention

The enterocyte-like cells obtained by the method for inducing differentiation of the present invention have high gene expression levels of a drug-metabolizing enzyme CYP3A4, which plays an important role in drug metabolism in the small intestine, a transporter PEPT1 (apical transporters, basolateral transporters), multidrug resistance protein 1 (MDR1: hereinafter referred to as "P-gp"), and breast cancer resistance protein (BCRP), and also have a tight junction function, and hence have properties close to enterocytes. The enterocyte-like cell of the present invention is excellent in terms of expression levels of the drug-metabolizing enzyme and the transporters as compared to hitherto generally used Caco-2 cells. As a result of the foregoing, it has become possible to efficiently generate enterocyte-like cells that enable simultaneous evaluation of drug metabolism and drug absorption. It has heretofore been difficult to acquire human primary enterocytes. However, the method for inducing differentiation of the present invention has enabled stable provision of excellent enterocyte-like cells. The method for inducing differentiation of the present invention is particularly excellent in that human enterocyte-like cells have been able to be generated.

Hitherto, it has been difficult to acquire primary enterocytes, particularly human primary enterocytes, and there have not existed excellent cells that reflect a model of normal human enterocytes and enable stable testing. However, enterocyte-like cells having properties closer to those of human enterocytes have been able to be generated.

BRIEF DESCRIPTION OF DRAWINGS

FIG. 1A is a diagram for illustrating a protocol for inducing differentiation from human ES/iPS cells to enterocyte-like cells by a related-art method, and FIG. 1B are a graph and photographs for showing results confirming differentiation induction efficiency (Comparative Example 1).

FIG. 2A is a diagram for illustrating a protocol for inducing differentiation from human iPS cells to enterocyte-like cells, and FIG. 2B is a graph for showing expression results of aminopeptidase N (ANPEP) in obtained cells (Example 2).

FIG. 3A is a diagram for illustrating a protocol for inducing differentiation from human iPS cells to enterocyte-like cells, and FIG. 3B is a graph for showing expression results of VILLIN in obtained cells (Example 2).

FIG. 4A is a diagram for illustrating a protocol for inducing differentiation from human iPS cells to enterocyte-like cells, and FIG. 4B is a graph for showing expression results of ANPEP in obtained cells (Example 3).

FIG. 5A is a diagram for illustrating a protocol for inducing differentiation from human iPS cells to enterocyte-like cells, and FIG. 5B is a graph for showing results confirming differentiation induction efficiency (Example 4).

FIG. 6A is a diagram for illustrating a protocol for inducing differentiation from human iPS cells to enterocyte-like cells, and FIGS. 6B, 6C, and 6D are graphs for showing expression results of transporters (PEPT1, OSTα, OSTβ, OCT1, MRP3, OATP-B, ASBT1, MCT1, MRP2, BCRP, and P-gp) in obtained cells (Example 5).

FIG. 7A is a diagram for illustrating a protocol for inducing differentiation from human iPS cells to enterocyte-like cells, FIG. 7B is a graph for showing the tight junction function of obtained cells, and FIG. 7C are photographs for showing expression results of ZO-1 in the obtained cells (Example 6-1).

FIG. 8A is a diagram for illustrating a protocol for inducing differentiation from human iPS cells to enterocyte-like cells, and FIG. 8B is a graph for showing expression results of a drug-metabolizing enzyme CYP3A4 in obtained cells (Example 6-2).

FIG. 9A is a diagram for illustrating a protocol for inducing differentiation from human iPS cells to enterocyte-like cells, and FIGS. 9B and 9C are graphs and images for showing results of the CYP3A4 induction potency of obtained cells. In FIG. 9B, vitamin D3 (hereinafter referred to as "VD3") is used as a CYP3A4 inducer, and in FIG. 9C, rifampicin (hereinafter referred to as "RIF") is used as a CYP3A4 inducer (Example 6-3).

FIG. 10A is a diagram for illustrating a protocol for inducing differentiation from human iPS cells to enterocyte-like cells by the introduction of FOXA2 gene and CDX2 gene, and FIG. 10B are graphs for showing expression results of small intestine-related genes (ANPEP, PEPT1, CYP3A4, OSTα, OSTβ, MRP2, and P-gp) in obtained cells (Example 7).

FIG. 11A is a diagram for illustrating a protocol for inducing differentiation from human iPS cells to enterocyte-like cells by the introduction of FOXA2 gene and CDX2 gene, and FIG. 11B is a graph for showing results confirming differentiation induction efficiency (Example 8).

FIG. 12A is a diagram for illustrating a protocol for inducing differentiation from human iPS cells to enterocyte-like cells by the introduction of FOXA2 gene and CDX2 gene, and FIGS. 12B and 12C are graphs for showing results of CYP3A4/P-gp induction potency of obtained cells. In FIG. 12B, VD3 is used as a CYP3A4/P-gp inducer, and in FIG. 12C, RIF is used as a CYP3A4/P-gp inducer (Example 9).

FIG. 17B is a graph for showing results confirming an interaction between the CYP3A4 inhibitor (GFJ) and the drug (AM) for the enterocyte-like cells (HiPS-ELC-TFs) (Example 12).

FIG. 18A is a graph for showing measurement results of the cell membrane resistance value (transepithelial electrical resistance: hereinafter referred to as "TEER") of enterocyte-like cells (HiPS-ELC-TFs). FIG. 18B is a graph for showing results confirming a Papp value by an FD4 (fluorescein isothiocyanate-dextran average mol wt 4,000) permeation test (Example 13).

DESCRIPTION OF EMBODIMENTS

Figure 13A:
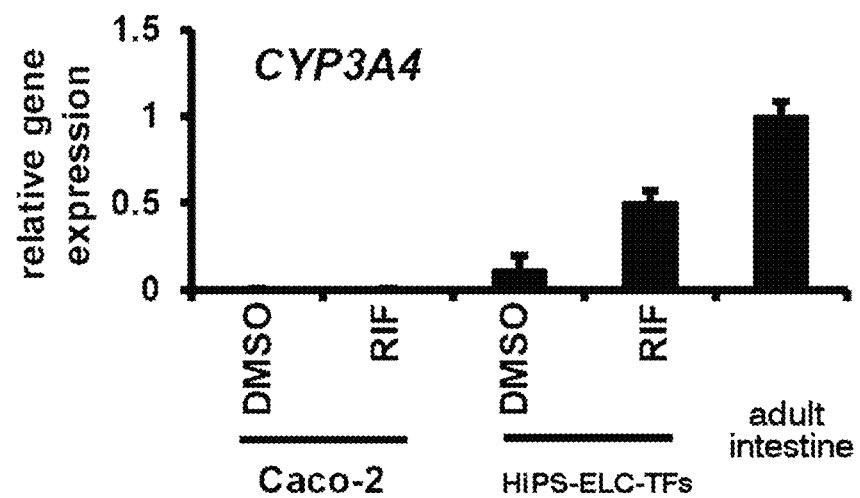
FIG. 13A is a graph for showing results confirming CYP3A4 expression for enterocyte-like cells (HiPS-ELC-TFs) and various cells. RIF is used as a CYP3A4 inducer.

The present invention relates to a selective method for inducing differentiation from pluripotent stem cells (PSCs) to enterocyte-like cells, and also relates to an excellent enterocyte-like cell expressing drug-metabolizing enzymes and drug transporters.

In order to predict the pharmacokinetics of a drug, it is extremely important to predict drug absorption in a small intestine. However, it is extremely difficult to acquire human primary enterocytes. Caco-2 cells are a human colon carcinoma-derived cell line and can form strong tight junctions, and hence are generally used as an in vitro absorption evaluation system serving as a model for predicting drug permeation in the small intestine. Meanwhile, a main drug-metabolizing enzyme in enterocytes is CYP3A4, but the Caco-2 cells hardly express drug-metabolizing enzymes unlike the human small intestine. Accordingly, the Caco-2 cells do not enable the evaluation of drug metabolism capacity. At present, an experimental system capable of simultaneously evaluating drug metabolism and drug absorption in the small intestine has yet to be constructed.

Among drug-metabolizing enzymes CYPs (Cytochromes P450), some molecular species (CYP1A2, CYP2B6, and CYP3A4) are known to have increased expression levels in response to a drug serving as an inducer. This phenomenon is called CYP induction. When the CYP induction is caused, a drug metabolism rate greatly changes from that under an uninduced state. CYP3A4, which is a main CYP molecular species in the small intestine, is induced by drugs such as VD3 and RIF. In view of the foregoing, the inventors of the present invention have aimed to generate enterocyte-like cells applicable to the evaluation of drug metabolism and drug absorption, from human pluripotent stem cells. The "enterocyte-like cells" as used herein mean cells generated by a method for inducing differentiation of the present invention or differentiation induction treatment.

The pluripotent stem cells as used herein only need to be undifferentiated cells having pluripotency and/or a self-replication ability, and are not particularly limited, but include pluripotent stem cells, for example, induced pluripotent stem cells (iPS cells) or embryonic stem cells (ES cells). Of those, iPS cells are particularly suitable.

The iPS cells refer to induced pluripotent stem cells having pluripotency and proliferative capacity similar to ES cells. The iPS cells were generated by inducing reprogramming of differentiated cells without use of fertilized eggs, surplus embryos, or ES cells by introducing several kinds of genes into somatic cells, and were established from mouse fibroblasts in 2006 for the first time in the world. Further, it has been reported that human iPS cells were successfully established by introducing four human genes OCT3/4, SOX2, KLF4, and C-MYC homologous to the four genes used in establishing mouse iPS cells into fibroblasts derived from humans (Cell 131: 861-872, 2007). The iPS cells to be used in the present invention may be iPS cells generated by such a known method per se as the above-mentioned method or may be iPS cells to be generated by a novel method developed in the future.

The ES cells are pluripotent stem cells obtained by transferring a cell mass called an inner cell mass, which is generally present in the embryo at the blastocyst stage, to in vitro culture, followed by isolation as a population of undifferentiated stem cells from the culture. The ES cells were established as a cell line having pluripotency in mice by M. J. Evans & M. H. Kaufman (Nature, 292, 154, 1981), and then by G. R. Martin (Natl. Acad. Sci. USA, 78, 7634, 1981). There are many human-derived ES cell lines already established and these cell lines can be obtained from, for example, ES Cell International, Wisconsin Alumni Research Foundation, National Stem Cell Bank (NSCB), and the like. The ES cells are generally established by culturing early embryos. The ES cells may also be generated from early embryos containing the nuclei of somatic cells transplanted. Alternatively, there is a method involving generating a cell structure like the embryo at the blastocyst stage by transplanting the cell nuclei of a desired animal into cell vesicles (cytoplasts or ooplastoids) generated by dividing egg cells or denucleated egg cells of a foreign animal into a plurality of pieces and generating ES cells based on the cell structure. In addition, there have been reported an attempt to generate ES cells by developing parthenogenetic embryos to the phase similar to the blastocyst stage and generating ES cells from the embryos and a method involving generating ES cells having genetic information on the nuclei of somatic cells by fusion of ES cells and somatic cells. The ES cells to be used in the present invention may be ES cells generated by such a known method per se as the above-mentioned method or may be ES cells to be generated by a novel method developed in the future.

It is necessary that the method for inducing differentiation from pluripotent stem cells to enterocyte-like cells of the present invention include the following steps:

1) inducing differentiation from pluripotent stem cells to definitive endoderm cells; and 2) culturing the definitive endoderm cells obtained by the inducing differentiation in a system containing anyone or more kinds of substances selected from an ALK5 inhibitor (SB431542), Wnt3a, and EGF.

3) The method may further include a step of introducing CDX2 gene and/or FOXA2 gene during any one of the step 1) or the step 2). With this, the enterocyte-like cells can be generated with an efficiency of 80% or more.

4) The method may further include a step of overlaying abasement membrane matrix during the step 2). With this, the gene expression level of a small intestinal epithelial marker can be increased.

As a method for inducing differentiation from the pluripotent stem cells to the definitive endoderm cells in the step 1) in the generation of the enterocyte-like cells, a known method per se may be applied. For example, a humoral factor or a compound, such as Activin A, Wnt3a, a GSK3β inhibitor, sodium butyrate, basic fibroblast growth factor (bFGF), bone morphogenetic protein 4 (BMP4), Ly294002, or dimethyl sulfoxide (DMSO), may be used in the culture system of the pluripotent stem cells, and Activin A may be particularly suitably used. The addition amount of the humoral factor or the compound only needs to be such that the differentiation from the pluripotent stem cells to the definitive endoderm cells can be induced, and is not particularly limited. For example, in the case of Activin A, 3 ng/ml to 200 ng/ml thereof, preferably about 100 ng/ml thereof may be added to the culture system. It is considered that, when the concentration of Activin A is less than 3 ng/ml, differentiation to endoderm cannot be efficiently promoted. The timing at which the humoral factor or the compound is added to the culture system only needs to be such timing that the differentiation from the pluripotent stem cells to the definitive endoderm cells can be induced, and is not particularly limited. For example, the humoral factor or the compound may be added during a period from day 0 to day 6 after the initiation of the culture of the pluripotent stem cells, preferably for 4 days.

In the present invention, in the generation of the enterocyte-like cells, it is necessary that differentiation from the definitive endoderm cells to the enterocyte-like cells be induced in the step 2). As a method of inducing the differentiation from the definitive endoderm cells to the enterocyte-like cells, there is given, for example, a method involving adding a humoral factor or a compound, such as BIO or DAPT, to the culture system of the definitive endoderm cells as disclosed in Non Patent Literature 3. For example, in the case of BIO, 0.01 μM to 10 μM thereof, preferably about 5 μM thereof may be added to the culture system. When the concentration of BIO is less than 0.01 μM, there is a risk in that its promoting effect on the differentiation to the enterocyte-like cells cannot be confirmed. When the concentration of BIO is more than 10 μM, there may be a risk in that cytotoxicity occurs. For example, in the case of DAPT, 0.02 μM to 20 μM thereof, preferably about 10 μM thereof may be added to the culture system. When the concentration of DAPT is less than 0.02 µM, there may be a risk in that its promoting effect on the differentiation to the enterocyte-like cells cannot be confirmed. The timing at which BIO and DAPT are added to the culture system only needs to be such timing that the differentiation from the definitive endoderm cells to the enterocyte-like cells can be induced, and is not particularly limited. For example, BIO and DAPT may be added during a period from day 0 to day 30 after the initiation of the culture of the definitive endoderm cells, preferably for 30 days. Any one of BIO and DAPT may be added first, or BIO and DAPT may be simultaneously added.

The method for inducing differentiation from pluripotent stem cells to enterocyte-like cells of the present invention has a feature of adding an additional compound to the culture system at the time of inducing differentiation from the definitive endoderm cells to the enterocyte-like cells using BIO and/or DAPT described above in the step 2) in the generation of the enterocyte-like cells. An example of the additional compound is any one or more kinds of compounds selected from an ALK5 inhibitor (SB431542), Wnt3a, and EGF. For example, in the case of SB431542, 0.02 µM to 20 µM thereof, preferably about 10 µM thereof may be added to the culture system. For example, in the case of Wnt3a, 0.1 nM to 10 mM thereof may be added to the culture system. When the concentration of SB431542 is less than 0.02 µM, there may be a risk in that its promoting effect on the differentiation to the enterocyte-like cells cannot be confirmed. For example, in the case of EGF, 10 ng/ml to 1,000 ng/ml thereof, preferably about 250 ng/ml thereof may be added to the culture system. With regard to the timing at which any one or more kinds selected from SB431542, Wnt3a, and EGF are added to the culture system, the addition may be performed before or after, or simultaneously with, the addition of the substance, such as BIO and/or DAPT, to be added at the time of inducing differentiation from the definitive endoderm cells to the enterocyte-like cells. For example, any one or more kinds selected from SB431542, Wnt3a, and EGF may be added during a period from day 15 to day 30 after the initiation of the culture of the definitive endoderm cells, preferably for 15 days.

In the steps 1) and 2), when an Ad vector carrying CDX2 gene and/or FOXA2 gene is introduced into the cells as in Patent Literature 1, the efficiency of the induction of the differentiation to the enterocyte-like cells can be further improved. For example, in the step 1), the FOXA2 gene may be introduced into the definitive endoderm cells obtained by differentiation induction from the pluripotent stem cells, such as ES cells or iPS cells, and in the step 2), the CDX2 gene may be introduced into the definitive endoderm cells obtained by the differentiation induction. Specifically, the pluripotent stem cells are cultured, for example, in a medium containing Activin A, and the cells may be subjected to the action of Ad-FOXA2 carrying the FOXA2 gene. After that, for example, the cells are cultured again in a medium containing Activin A and cultured in a medium containing BIO and DAPT, and then the cells may be subjected to the action of Ad-CDX2 carrying the CDX2 gene. After that, the cells may be cultured in a medium containing BIO and DAPT, and SB431542, EGF, and Wnt3a.

The CDX2 gene and/or the FOXA2 gene may also be introduced into mesendoderm cells, definitive endoderm cells, small intestinal stem cells, or small intestinal progenitor cells generated by differentiating pluripotent stem cells, such as ES cells or iPS cells, with a differentiation inducer other than the CDX2 gene or the FOXA2 gene. For example, the CDX2 gene and/or the FOXA2 gene may also be introduced into any of various cells generated by a method disclosed in Patent Literature 3 or 4. It is considered that, besides CDX2 and FOXA2, genes involved in the differentiation/proliferation of enterocytes, such as FOXA1, FOXA3, GATA4, GATA6, CDX1, Hes1, Math1, Tcf1, LEF1, Tcf-3, Tcf-4, HNF4α, HNF1α, SOX9, KLF5, KLF4, and Ascl2, can be introduced to efficiently generate enterocyte-like cells from ES cells or iPS cells. A step of introducing each of the genes may be appropriately selected depending on the degree of differentiation of the cells.

In the present invention, the Ad vector is not particularly limited, and an Ad vector generated by a known method per se may be used. For example, the Ad vector may be an improved Ad vector obtained by improving an Ad vector so as to allow its introduction even into cells expressing no Ad receptor or expressing an Ad receptor at an extremely low level, or may be an Ad vector usable for cells expressing an Ad receptor. Specifically, an Ad vector having introduced therein: DNA encoding a cell adhesive peptide (RGD sequence), which is a typical adhesive peptide; DNA encoding a peptide having an affinity for heparan sulfate, for example, K7 (KKKKKKK: SEQ ID NO: 1); DNA encoding a peptide having an affinity for a laminin receptor; DNA encoding a peptide having an affinity for E-selectin; DNA encoding a peptide having an affinity for an integrin; or the like may be used. For example, an Ad vector disclosed in Patent Literature 1 may be used.

With regard to the genes to be introduced, as the CDX2 gene, for example, one registered with GENBANK Accession No. NM_001265 may be used, and as the FOXA2 gene, for example, one registered with GENBANK Accession No. NM_021784 may be used.

The cells obtained by adding the humoral factor and/or the compound necessary for differentiation induction to the culture system in the steps 1) and 2) may be cultured for about 34 days or more after the initiation of the culture of the pluripotent stem cells.

As a culture medium that may be used in the present invention, for example, culture media listed below may be used. The amount of a substance to be added to each culture medium may be appropriately increased or decreased depending on a purpose. The manufacturers/distributors of a reagent to be used are not limited to those described below as long as the reagent can exhibit a function equivalent to that described below.

(A) As a medium for maintaining an undifferentiated state of human ES/iPS cells, a medium for maintaining various types of stem cells including REPROSTEM (product name), IPSELLON (product name), ESSENTIAL 8 (product name), TESR-E8 (product name), and the like supplemented with bFGF and the like may be used.

(B) As a medium for differentiation induction, a medium containing HESF-GRO (product name, CELL SCIENCE & TECHNOLOGY INSTITUTE, INC.), which is an essential medium for culturing ES cells, supplemented with insulin (10 µg/ml), transferrin (5 µg/ml), 2-mercaptoethanol (10 µM), 2-ethanolamine (10 µM), sodium selenite (20 nM), and bovine serum albumin (BSA: 1 mg/ml) may be used. As another mode of the medium for differentiation induction, a medium (FASEB J. 23:114-22 (2009)) containing HESF-DIF (product name, CELL SCIENCE & TECHNOLOGY INSTITUTE, INC.), which is an essential medium for differentiation induction of ES cells, supplemented with insulin (10 µg/ml), transferrin (5 µg/ml), 2-mercaptoethanol (10 µM), 2-ethanolamine (10 µM), and sodium selenite (20 nM) may be used.

(C) As another mode of the medium for differentiation induction, a medium containing a RPMI1640 MEDIUM (SIGMA ALDRICH CO. LLC.) supplemented with 4 mM L-Glutamine, B27 SUPPLEMENT (INVITROGEN), and penicillin/streptomycin may also be used. Media to be used when definitive endoderm cells are subjected to differentiation induction are not limited to those described above as long as the media can exhibit equivalent functions.

(D) For the induction of differentiation from and after the definitive endoderm cells, a differentiation DMEM-high Glucose medium, a differentiation DMEM-high Glucose medium (INVITROGEN) containing 10% KNOCKOUT Serum Replacement (INVITROGEN), 1% Non Essential Amino Acid Solution (INVITROGEN), penicillin/streptomycin, 2 mM L-Glutamine, and 100 µmol/l β-mercaptoethanol) may be used.

In the steps of the method for inducing differentiation of the present invention, the cells being cultured may be overlaid with a solution containing a basement membrane matrix and further cultured. The basement membrane matrix is a supramolecular structure present extracellularly in organisms, and is also called an extracellular matrix (ECM) and abbreviated as ECM. An example of the basement membrane matrix that may be used in the method of the present invention is MATRIGEL (product name), which is a commercially available "soluble basement membrane extracted from the Engelbreth-Holm-Swarm (EHS) mouse sarcoma." The basement membrane matrix or the like may be overlaid on a culture substrate by a known method per se or a method to be developed in the future. As the culture substrate, such as a culture vessel, to be used for the culture of the cells of the present invention, a culture substrate coated with the basement membrane matrix or the like may be used to perform culture.

Figure 21:
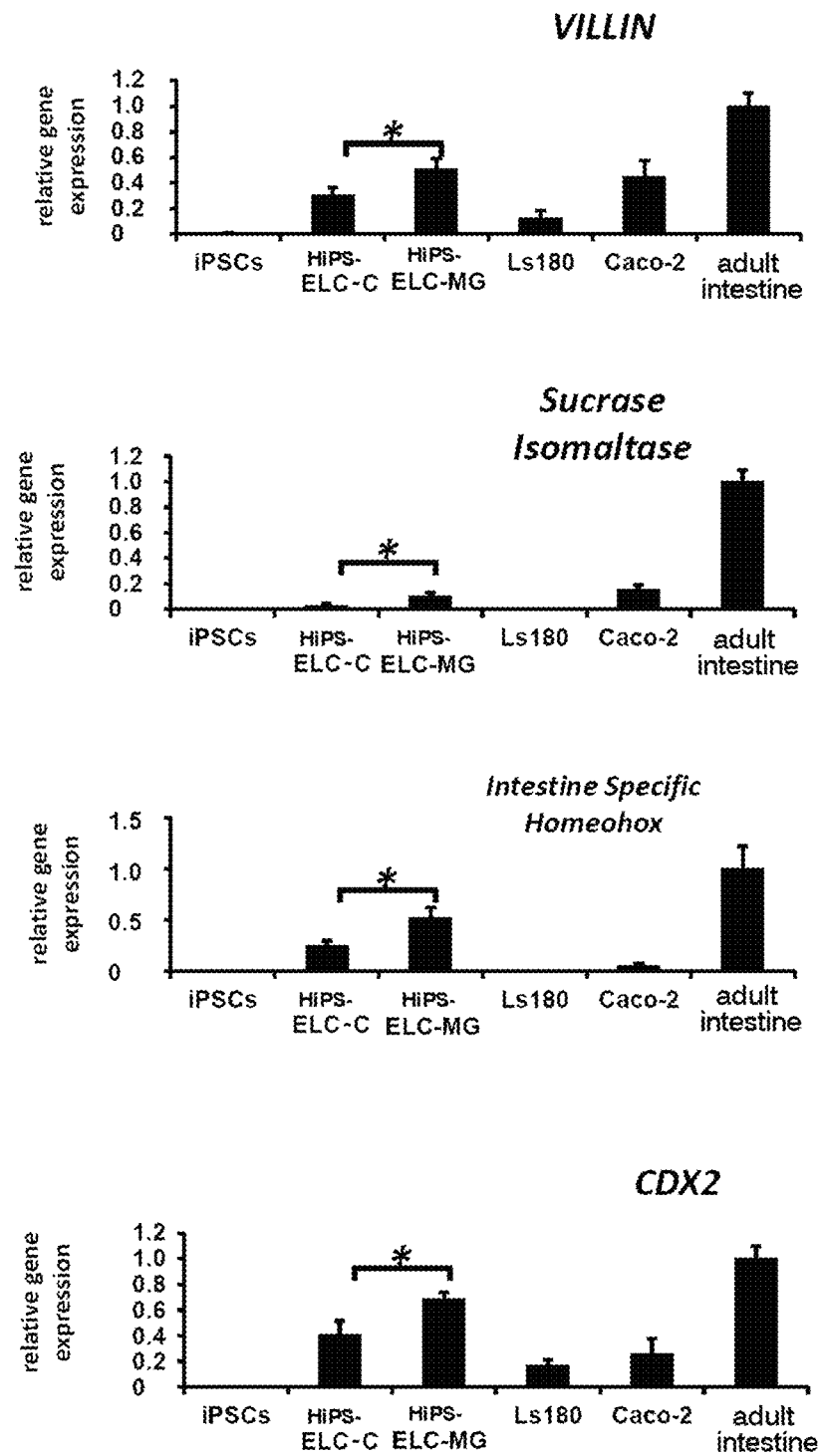
FIG. 21 are graphs for showing results of analysis of the gene expression of each of small intestine-related genes VILLIN, SI, Intestine Specific Homeobox, and CDX2 for enterocyte-like cells (HiPS-ELC-MGs) and various cells (Experimental Example 15-1).

For example, during a period from 24 hours to 1 hour before the initiation of differentiation, a dilution of MATRIGEL 100-fold diluted with an essential medium for differentiation induction at 4° C. is overlaid on the culture substrate, the solution not attached to the culture substrate is removed at the time of the initiation of differentiation induction treatment, and then the resultant may be used as a culture substrate for differentiation induction. In addition, when Matrigel is used during the differentiation induction treatment, it is suitable that, on day 25 of differentiation induction to the enterocyte-like cells, a dilution of MATRIGEL 100-fold diluted with a differentiation induction medium (differentiation DMEM-high Glucose medium) at 16° C. be overlaid on the enterocyte-like cells. When MATRIGEL is overlaid during the differentiation, the differentiation to the enterocyte-like cells is promoted (FIG. 21).

An enterocyte-like cell obtained by the method for inducing differentiation of the present invention is an enterocyte-like cell obtained from a pluripotent stem cell by artificially performing differentiation induction treatment. The enterocyte-like cell expresses a drug-metabolizing enzyme and/or a drug transporter. Specifically, the enterocyte-like cell of the present invention is positive for enterocyte markers VILLIN and CDX2. Further, in the enterocyte-like cell of the present invention, the expression levels of a drug-metabolizing enzyme CYP3A4, a transporter PEPT1, and the like show significantly high values as compared to even those in Caco-2 cells generally used as an intestinal epithelial cell model, and show values close to those in the human small intestine. In addition, enterocytes strongly join together to form tight junctions, and the enterocyte-like cells obtained by the method for inducing differentiation of the present invention also have an excellent tight junction function in terms of measurement values for TEER and Zonula (Zona) occludens 1 protein (ZO-1, also called Tight-junctionprotein-1: TJP-1), which is one kind of scaffold protein for tight junctions. The present invention also encompasses an enterocyte-like cell obtained by the method for inducing differentiation. Further, the present invention also encompasses a culture product, which is obtained from the above-mentioned pluripotent stem cells through artificial treatment by the method for inducing differentiation and culture.

The present invention also encompasses a evaluation method for drug-induced toxicity and/or a evaluation method for pharmacokinetics, including using the enterocyte-like cell obtained by the above-mentioned method for inducing differentiation. Further, the present invention also encompasses a method for drug-drug interaction test and a CYP induction assay, including using the enterocyte-like cell. Through the addition of a pharmaceutical candidate compound to the enterocyte-like cell obtained as described above, the pharmaceutical candidate compound can be tested and evaluated for each of drug metabolism/drug absorption, drug toxicity and/or pharmacokinetics, a drug-drug interaction, drug-metabolizing enzyme induction, and the like. Hitherto, human primary enterocytes have been difficult to acquire, and have had a problem of differences in properties due to individual differences. However, the method for inducing differentiation of the present invention enables stable provision of excellent enterocyte-like cells.

EXAMPLES

Now, the present invention is specifically described by way of Examples and Experimental Examples for further understanding of the present invention. However, it should be appreciated that the scope of the present invention is by no means limited to these Examples.

Reference Example 1

Compositions of Various Types of Media

Various types of media are required for human iPS cells or human ES cells in the culture method shown in Examples of the present invention. In Reference Example 1, compositions of culture media that may be used for various types of cultures are described.

(A) As a medium for maintaining an undifferentiated state of human ES/iPS cells, a medium for maintaining various types of stem cells including REPROSTEM (product name), IPSELLON (product name), ESSENTIAL 8 (product name), TESR-E8 (product name), and the like supplemented with bFGF may be used. The medium is hereinafter referred to as "medium 1".

(B) As a medium for differentiation induction, a medium containing HESF-GRO (product name, CELL SCIENCE & TECHNOLOGY INSTITUTE, INC.), which is an essential medium for culturing ES cells, supplemented with insulin (10 µg/ml), transferrin (5 µg/ml), 2-mercaptoethanol (10 µM), 2-ethanolamine (10 µM), sodium selenite (20 nM), and BSA (1 mg/ml) may be used. As another mode of the medium for differentiation induction, a medium (FASEBJ. 23:114-22 (2009)) containing HESF-DIF (product name, CELL SCIENCE & TECHNOLOGY INSTITUTE, INC.), which is an essential medium for differentiation induction of ES cells, supplemented with insulin (10 µg/ml), transferrin (5 µg/ml), 2-mercaptoethanol (10 µM), 2-ethanolamine (10 µM), and sodium selenite (20 nM) may also be used.

(C) As another mode of the medium for differentiation induction, a medium containing a RPMI1640 MEDIUM (SIGMA ALDRICH CO. LLC.) supplemented with 4 mM L-Glutamine, B27 SUPPLEMENT (INVITROGEN), and penicillin/streptomycin may also be used. The medium is hereinafter referred to as "medium 2". Media to be used when definitive endoderm cells are subjected to differentiation induction are not limited to those described above as long as the media can exhibit equivalent functions.

(D) For the induction of differentiation from and after the definitive endoderm cells, a differentiation DMEM-high Glucose medium (differentiation DMEM-high Glucose medium (INVITROGEN) containing 10% KNOCKOUT Serum Replacement (INVITROGEN), 1% Non Essential Amino Acid Solution (INVITROGEN), penicillin/streptomycin, 2 mM L-Glutamine, and 100 µmol/l β-mercaptoethanol) may be used. The "differentiation DMEM-high Glucose medium" is hereinafter referred to as "medium 3".

Example 1

Generation of Definitive Endoderm Cells

In this Example, the generation of definitive endoderm cells to be used in the following Comparative Example and Examples is described. The definitive endoderm cells were generated using human iPS cells or human ES cells as pluripotent stem cells. In this Example, Tic (JCRB1331) was used as a human iPS cell line. A human ES cell line (KhES3) was handled in accordance with the guidelines of the Ministry of Education, Culture, Sports, Science and Technology, and experiments were performed with the approval of an ethics committee. The pluripotent stem cells were cultured using the medium 1 as feeder cells in accordance with a method described in Tiss. Cult. Res. Commun., 27: 139-147 (2008).

Differentiation induction treatment was performed by adding 100 ng/ml Activin A to the culture system of the human iPS cell line (Tic) and culturing the cells for 4 days. Thus, definitive endoderm cells for generating enterocyte-like cells in the following Examples and Comparative Example were generated.

Comparative Example 1

Generation of Enterocyte-Like Cells by Related-Art Method for Inducing Differentiation In this Comparative Example, BIO (5 µM) and DAPT (10 µM) were added to a culture system of the definitive endoderm cells generated from the human iPS cell line (Tic) or the human ES cell line (K3) by the method described in Example 1 above, and the cells were cultured for 20 days using the medium 3 (FIG. 1A). The method of this Comparative Example is based on a method disclosed in Non Patent Literature 3.

For cells obtained on day 24 after the initiation of the culture of Tic or K3, the efficiency of the induction of differentiation to enterocyte-like cells was evaluated with the use of the expression of VILLIN, a constituent protein of a microvillus, as an indicator. The expression ratio of VILLIN was measured by FACS analysis. The results were as follows: about 20% of Tic-derived cells were VILLIN-positive cells, and about 3% of K3-derived cells were VILLIN-positive cells. A fluorescent staining method also confirmed similar degrees of VILLIN expression (FIG. 1B). Thus, it was confirmed that the obtained cells were enterocyte-like cells.

The FACS analysis was performed by the following method. The cells subjected to the treatment for inducing differentiation to the enterocyte-like cells described above were detached, and then subjected to cell permeation treatment with 1× Permeabilization Buffer (E-BIOSCIENCE) for 30 minutes. The cells were labeled with a primary antibody and a secondary antibody, and the FACS analysis was performed using a FACS LSR FORTESSA flow cytometer (BD Biosciences).

Example 2

Investigation of Method for Inducing Differentiation Using Enterocyte Markers (ANPEP and VILLIN) as Indicators In this Example, with the use of enterocyte markers ANPEP and VILLIN as indicators, a method for inducing differentiation in which an improvement was made over the method for inducing differentiation of Comparative. Example was attempted.

The definitive endoderm cells generated from the human iPS cell line (Tic) by the method described in Example 1 above were further cultured for 15 days using the medium 3. During a period from day 4 to day 19 after the initiation of differentiation induction, BIO (5 µM) and DAPT (10 µM) were added to the culture system. Simultaneously with the addition of the BIO and the DAPT, the cells were further cultured for 5 days using the medium 3 supplemented with any one of phorbol-myristate-acetate (PMA), transforming growth factor β1 (TGEβ1), Wortmannin, Noggin, SB431542, Follistatin, EGF, R-spondin1, Pentagastrin, or Wnt3a (FIG. 2A and FIG. 3A).

With regard to the measurement of the enterocyte markers ANPEP and VILLIN, each of the enterocyte markers was measured by a quantitative real-time RT-PCR method using SYBR Green gene expression assays (APPLIED BIOSYSTEMS). When a system in which culture was performed without the addition of the compounds was used as a control, the expression of ANPEP showed a high value in the system in which culture was performed with the addition of PMA, Wortmannin, SB431542, EGF, or Wnt3a (FIG. 2B), and the expression of VILLIN showed a high value in the system to which SB431542, EGF, or Wnt3a was added (FIG. 3B). Thus, high expressions of ANPEP and VILLIN were found when the cells were cultured in the system containing SB431542, EGF, or Wnt3a.

The quantitative real-time RT-PCR was performed by the following method. With the use of ISOGEN (NIPPON GENE), total RNA was collected from the enterocyte-like cells obtained by differentiation induction from the human iPS cells. Each total RNA was treated with RNase-free DNaseI (NEW ENGLAND BIOLABS), and then subjected to a reverse transcription reaction using SUPERSCRIPT VILO cDNA Synthesis Kit (INVITROGEN) to synthesize complementary DNA (cDNA). As a positive control, the total RNA (CLONTECH, BIOCHAIN four lots in total) of a human adult small intestine (human adult intestine: hereinafter sometimes referred to as "AI") tissue to be used was similarly subjected to cDNA synthesis. A quantitative real-time RT-PCR method using SYBR Green gene expression assays (APPLIED BIOSYSTEMS) was performed, and quantification was performed with STEPONEPLUS real-time PCR System (APPLIED BIOSYSTEMS).

Example 3

Investigation of Period for Inducing Differentiation Using Enterocyte Marker (ANPEP) as Indicator In this Example, with the use of an enterocyte marker ANPEP as an indicator, differentiation induction effects in the cases of different culture periods were confirmed.

The definitive endoderm cells generated from the human iPS cells by the method described in Example 1 above were cultured for 15 days in a system containing BIO (5 μM) and DAPT (10 μM) using the medium 3, and BIO (5 μM) and DAPT (10 μM), and SB431542 (10 μM), EGF (250 ng/ml), and Wnt3a were further added to the culture system. Then, after further culture for 5 days (from day 19 to day 24 after the initiation of culture), for 10 days (from day 19 to day 29 after the initiation of culture), or for 15 days (from day 19 to day 34 after the initiation of culture), cells were obtained (FIG. 4A). In the following Examples, the cells obtained from the human iPS cell line by the method for inducing differentiation of the present invention are referred to as "HiPS-ELCs" for convenience. In addition, when the HiPS-ELCs in the following Examples are distinguished from each other on the basis of the culture period, the number of days after the initiation of the culture of the pluripotent stem cells is specified.

For the HiPS-ELCs, the expression of the enterocyte marker ANPEP was measured by a real-time PCR method by the same procedure as in Example 2. The expression level of ANPEP in each case was significantly high in the HiPS-ELCs on day 34 of culture as compared to that in the HiPS-ELCs on day 24 or day 29 of culture, and showed a value close to that in the human small intestine (FIG. 4B). Thus, it was confirmed that the enterocyte marker was more effectively expressed by extending the culture period to 34 days. The value for the human small intestine was confirmed from commercially available total RNA of adult small intestine (four donors).

Example 4

Investigation of Method for Inducing Differentiation Using Enterocyte Marker (VILLIN) as Indicator In this Example, with the use of an enterocyte marker VILLIN as an indicator, the influences of the presence or absence of the actions of SB431542, EGF, and Wnt3a, and a change in culture period on differentiation induction efficiency were confirmed.

The definitive endoderm cells generated from the human iPS cells by the method described in Example 1 above were cultured for 15 days in a system containing BIO (5 μM) and DAPT (10 μM) using the medium 3, and BIO (5 μM) and DAPT (10 μM), and SB431542 (10 μM), EGF (250 ng/ml), and Wnt3a were further added to the culture system. As a control, a group in which SB431542 (10 μM), EGF (250 ng/ml), and Wnt3a were not added to the culture system was also prepared. Then, the cells were further cultured for 5 days (from day 19 to day 24 after the initiation of culture) or for 15 days (day 19 to day 34 after the initiation of culture) to generate HiPS-ELCs by differentiation induction (FIG. 5A).

For the HiPS-ELCs on day 24 and day 34 of culture, VILLIN positive rates were measured by FACS. In each case, the culture system containing none of SB431542, EGF, and Wnt3a was used as a control. The results found that, in the system containing the compounds, the VILLIN positive rate reached 40% on day 34 of culture (FIG. 5B). Thus, it was demonstrated that the efficiency of differentiation to enterocyte-like cells was able to be improved by using the three kinds of compounds and performing culture during the period from day 19 to day 34 after the initiation of culture.

Example 5

Expression of Drug-Metabolizing Enzyme and Transporter

In this Example, for the HiPS-ELCs, the gene expression of a transporter (PEPT1) was confirmed, and the drug metabolism capacity of the HiPS-ELCs was confirmed. In particular, PEPT1, P-gp, and BCRP are each a transport protein playing an important role in drug transport in the small intestine.

The definitive endoderm cells generated from the human iPS cells by the method described in Example 1 above were cultured for 15 days in a system containing BIO (5 μM) and DAPT (10 μM) using the medium 3, and BIO (5 μM) and DAPT (10 μM), and SB431542 (10 μM), EGF (250 ng/ml), and Wnt3a were further added to the culture system. Then, the cells were further cultured for 15 days (from day 19 to day after the initiation of culture) to generate HiPS-ELCs by differentiation induction (FIG. 6A).

For the HiPS-ELCs on day 34 of culture, the expression level of PEPT1 gene was measured. For comparison to the expression level of the PEPT1 gene in hitherto generally used Caco-2 cells serving as a control, values for the HiPS-ELCs of this Example and the human adult small intestine were measured. As a result, the HiPS-ELCs were confirmed to have a high gene expression level of the transporter PEPT1, provide cells having properties close to those of human adult small intestine cells, and have the function of enterocytes (FIG. 6B). Further, with regard to the HiPS-ELCs on day 34 of culture, the gene expression levels of apical transporters and basolateral transporters were measured. As a result, in the HiPS-ELCs, the gene expression levels of the apical transporters and the basolateral transporters showed values close to those in the human adult small intestine, and thus the HiPS-ELCs were confirmed to have the function of enterocytes (FIGS. 6C and 6D).

Example 6-1

Confirmation of Tight Junction Function

It is known that enterocytes strongly join together to form tight junctions. In this Example, the tight junction function of the HiPS-ELCs was confirmed. In this Example, in the same manner as in Example 5, the definitive endoderm cells generated from the human iPS cells were cultured for 15 days in a system containing BIO (5 μM) and DAPT (10 μM) using the medium 3, and BIO (5 μM) and DAPT (10 μM), and SB431542 (10 μM), EGF (250 ng/ml), and Wnt3a were further added to the culture system. Then, the cells were further cultured for 15 days (from day 19 to day 34 after the initiation of culture) to generate HiPS-ELCs of this Example by differentiation induction (FIG. 7A).

The tight junction function was confirmed by measuring TEER. As a result, the HiPS-ELCs showed a cell membrane resistance value of 240 Ω·cm² on day 34 of culture, and were thus confirmed to have a tight junction function (FIG. 7B). Further, confirmation was made also for ZO-1, one kind of scaffold protein for tight junctions, and as a result, its expression was confirmed in the HiPS-ELCs of this Example as well (FIG. 7C), suggesting that tight junctions were formed.

Example 6-2

Confirmation of Expression of CYP3A4 Gene

In this Example, the expression of CYP3A4 gene in the HiPS-ELCs was confirmed. Human iPS cells were treated by the same procedure as in Example 6-1 (FIG. 8A).

For the HiPS-ELCs on day 34 of culture, the expression level of CYP3A4 gene was measured. For comparison to the expression level of the CYP3A4 gene in hitherto generally used Caco-2 cells serving as a control, values for the HiPS-ELCs of this Example and the human adult small intestine were measured. As a result, the HiPS-ELCs were confirmed to have a higher gene expression level of the drug-metabolizing enzyme PEPT1 than that in the Caco-2 cells, provide cells having properties close to those of the human adult small intestine, and have the function of enterocytes (FIG. 8B).

Example 6-3

Confirmation of Expression of CYP3A4 Gene (A) In this Example, the expression of CYP3A4 gene in the HiPS-ELCs was confirmed. Human iPS cells were treated by the same procedure as in Example 6-1 (FIG. 9A).

(B) For the HiPS-ELCs on day 34 of culture, the expression level of CYP3A4 gene was measured. VD3 or a solvent (DMSO) was used as a CYP3A4 inducer. When VD3 (100 nM) was allowed to act, the CYP3A4 gene expression level increased about 100-fold in the HiPS-ELCs as compared to that in the DMSO action group. In addition, when VD3 was allowed to act, the CYP3A4 protein expression level also increased (FIG. 9B).

(C) For the HiPS-ELCs on day 34 of culture, RIF or a solvent (DMSO) was used as a CYP3A4 inducer. When RIF (20 μM) was allowed to act, the CYP3A4 gene expression level increased about 8-fold in the HiPS-ELCs as compared to that in the DMSO action group. In addition, when RIF was allowed to act, the CYP3A4 protein expression level also increased (FIG. 9C).

From the foregoing, it was suggested that the HiPS-ELCs had CYP3A4 induction potency for a drug such as VD3 or RIF.

As described above, the cells obtained by the method for inducing differentiation described in Examples 4 to 6, that is, the "HiPS-ELCs" express markers expressed by enterocytes, express a drug-metabolizing enzyme and transporters, and also have a tight junction function, and hence can be said to be "enterocyte-like cells."

Example 7

Confirmation of Promoting Effect on Differentiation from Human iPS Cells to Enterocyte-Like Cells In this Example, in order to promote differentiation from human iPS cells to enterocyte-like cells, the genes of transcription factors involved in differentiation were introduced into cells during differentiation.

(A) Human iPS cells were cultured in the medium 2 containing 100 ng/ml Activin A for 2 days. On day 2 of culture, the cells were subjected to the action of Ad-FOXA2 carrying FOXA2 gene at 3,000 VP/cell for 90 minutes. For 2 days after that, the cells were cultured again in the medium 2 containing 100 ng/ml Activin A. During a period from day 4 to day 8 of culture, the cells were cultured in the medium 3 containing BIO (5 μM) and DAPT (10 μM). In addition, on day 8 of culture, the cells were subjected to the action of Ad-CDX2 carrying CDX2 gene at 3,000 VP/cell for 90 minutes. For 11 days after that, the cells were cultured in the medium 3 containing BIO (1 μM) and DAPT (2.5 μM). During a period from day 19 to day 34 of culture, the cells were cultured in the medium 3 containing BIO (1 μM) and DAPT (2 μM), and SB431542 (2 μM), EGF (250 ng/mL), and Wnt3a (FIG. 10A).

(B) In order to investigate whether or not differentiation to enterocyte-like cells was promoted by gene transfer, the expression levels of small intestine-related genes in FOXA2 gene and CDX2 gene-transferred cells (HiPS-ELC-TFs) and control cells (HiPS-ELC-LacZs) were analyzed by a real-time RT-PCR method. ANPEP, PEPT1, OSTα, OSTβ, MRP2, and P-gp are transporters, and CYP3A4 is a drug-metabolizing enzyme. The gene expression levels of ANPEP, PEPT1, CYP3A4, OSTα, and OSTβ in the HiPS-ELC-TFs were significantly high as compared to those in the HiPS-ELC-LacZs (FIG. 10B). Therefore, it is suggested that the introduction of the FOXA2 gene and the CDX2 gene promoted differentiation from human iPS cells to enterocyte-like cells.

Generation of Ad Vector

An Ad vector was generated by an in vitro ligation method. A FOXA2 gene or CDX2 gene expression shuttle plasmid in which the FOXA2 gene or the CDX2 gene was inserted into the multiple cloning site of a shuttle plasmid pHMEF5 was generated. With regard to the genes to be introduced, as the FOXA2 gene, for example, one registered with GENBANK Accession No. NM_021784 was used, and as the CDX2 gene, for example, one registered with GEN-BANK Accession No. NM_001265 was used.

Next, the shuttle plasmid was digested with I-CeuI and PI-SceI, and was inserted into a conventional-type vector plasmid pAdHM41K7 digested with the same enzymes, to thereby generate pAdHM41K7-EF-FOXA2 or pAdHM41K7-EF-CDX2. The generated Ad vector plasmid was digested with PacI, and was transfected into 293 cells using LIPOFECTAMINE 2000 (INVITROGEN), to thereby generate AdHM41K7-EF-FOXA2 (Ad-FOXA2) or AdHM41K7-EF-CDX2 (Ad-CDX2). The Ad vector was grown and purified by conventional methods. The physical titer (particle titer) of the Ad vector was measured by the method of Maizel et al.

A vector for LacZ gene transfer, AdHM41K7-EF-LacZ (Ad-LacZ), was generated by the same respective procedures.

Example 8

Investigation of Efficiency of Differentiation from Human iPS Cells to Enterocyte-Like Cells In this Example, the efficiency of differentiation from human iPS cells to enterocyte-like cells was analyzed.
(A) Human iPS cells were treated by the same procedure as in Example 7(A) (FIG. 11A).

(B) In order to evaluate the efficiency of differentiation to enterocyte-like cells, a VILLIN positive rate was measured on day 35 of differentiation induction using FACS. The introduction of the FOXA2 gene and the CDX2 gene increased the VILLIN positive rate from 38% to 96%. From the foregoing, it was ascertained that the introduction of the FOXA2 gene and the CDX2 gene increased the efficiency of differentiation from the human iPS cells to the enterocyte-like cells (FIG. 11B).

Example 9

Confirmation of CYP3A4 and P-gp Induction Potency in Enterocyte-Like Cells

In this Example, CYP3A4 and P-gp induction potency in enterocyte-like cells generated by gene transfer was evaluated.
(A) Human iPS cells were treated by the same procedure as in Example 7(A) (FIG. 12A).
(B) VD3 was used as a CYP3A4 and P-gp inducer. When VD3 was allowed to act, CYP3A4 increased about 100-fold in the HiPS-ELC-LacZs, but increased only about 10-fold in the HiPS-ELC-TFs. Meanwhile, the P-gp induction potency in the HiPS-ELC-TFs was higher than that in the HiPS-ELC-LacZs (FIG. 12B). (FOXA2 gene and CDX2 gene-transferred cells=HiPS-ELC-TFs, control cells=HiPS-ELC-LacZs)
(C) RIF was used as a CYP3A4 and P-gp inducer. When RIF was allowed to act, CYP3A4 increased about 7-fold in the HiPS-ELC-LacZs, but increased only about 3-fold in the HiPS-ELC-TFs. Meanwhile, the P-gp induction potency in the HiPS-ELC-TFs was higher than that in the HiPS-ELC-LacZs (FIG. 12C). (FOXA2 gene and CDX2 gene-transferred cells=HiPS-ELC-TFs, control cells=HiPS-ELC-LacZs)

From the foregoing, it was suggested that the introduction of the FOXA2 gene and the CDX2 gene lowered the CYP3A4 induction potency, but increased the P-gp induction potency.

Example 10

Comparison of CYP3A4 Expression in Enterocyte-Like Cells

In this Example, for the enterocyte-like cells of the present invention (HiPS-ELC-TFs: human iPS cell-derived enterocyte-like cells having introduced therein the FOXA2 and CDX2 genes), a CYP3A4 gene expression level when the cells were subjected to the action of RIF (20 µM/0.1% DMSO) for 48 hours was measured. The enterocyte-like cells (HiPS-ELC-TFs) were generated by the same procedure as in Example 7. As control cells, Caco-2 cells were similarly subjected to measurement. The expression level of the gene was measured by a real-time RT-PCR method.

In the Caco-2 cells, a change in CYP3A4 gene expression level due to the RIF action was not found, but in the HiPS-ELC-TFs, a significant increase in CYP3A4 gene expression level due to the RIF action was able to be confirmed (FIG. 13A). The CYP3A4 gene expression level in the HiPS-ELC-TFs subjected to the action of RIF was substantially equivalent to that in the human adult small intestine (AI) tissue. In this example, the total RNA of the AI was used as a control. Human Adult Normal Tissue: Small Intestine (BIOCHAIN INSTITUTE) was used as the AI. From the foregoing, it was found that the CYP3A4 induction by RIF was not able to be confirmed in the Caco-2 cells, but the CYP3A4 induction by RIF was able to be confirmed in the HiPS-ELC-TFs.

Figure 13B:
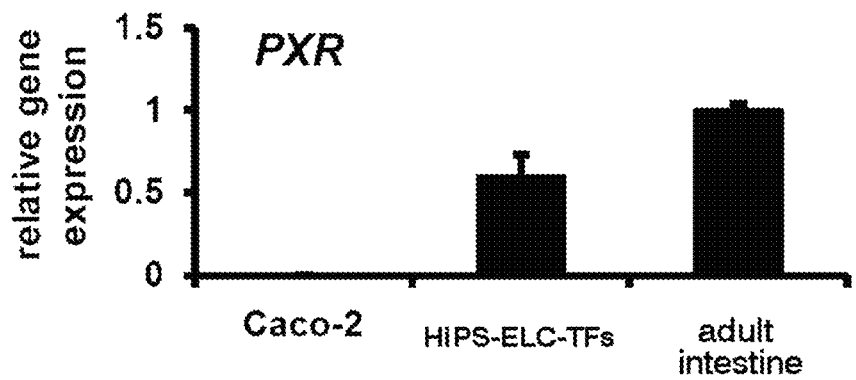
FIG. 13B is a graph for showing results confirming the expression of pregnane X receptor (PXR), which is one of nuclear receptors important for CYP3A4 induction in enterocyte-like cells (Example 10).

In the CYP3A4 induction, pregnane X receptor (PXR), one of nuclear receptors, plays an important role. In view of this, expression analysis of PXR in the Caco-2 cells and the HiPS-ELC-TFs was performed. The results found that the Caco-2 cells hardly expressed PXR, whereas the HiPS-ELC-TFs showed a PXR expression level corresponding to about 50% of that in the AI. Thus, it was suggested that, unlike the Caco-2 cells, the HiPS-ELC-TFs enabled the evaluation of PXR-mediated CYP3A4 induction (FIG. 13B).

Example 11

Confirmation of Drug Metabolism Capacity in Enterocyte-Like Cells

Figure 14:
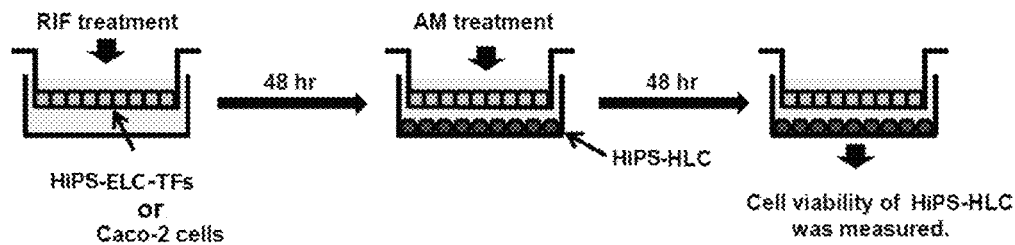
FIG. 14 is a diagram for illustrating an experimental method for the confirmation of the influence of a CYP3A4 inducer on drug metabolism in enterocyte-like cells (Example 11).

In this Example, with regard to CYP3A4 induced by drug stimulation of the enterocyte-like cells (HiPS-ELC-TFs) of the present invention, its influence on drug metabolism was confirmed. As a drug to be metabolized by CYP3A4, AM showing hepatotoxicity through metabolism was used. In the same manner as in Example 10, the HiPS-ELC-TFs were generated by the same procedure as in Example 7, and Caco-2 cells were used as a control. The HiPS-ELC-TFs or the Caco-2 cells were subjected to the action of RIF (20 µM/0.1% DMSO) for 48 hours, and then AM (25 µM, 50 µM, or 100 µM) was added to the medium. Simultaneously with the addition of AM, co-culture of the HiPS-ELC-TFs or the Caco-2 cells, and human iPS cell-derived hepatocytes (HiPS-HLCs) was initiated. After 48 hours, the cell viability of the HiPS-HLCs was measured (FIG. 14). The cell viability was measured using a WST-8 assay kit (DOJINDO). The cell viability of the DMSO action group was defined as 100%. The use concentration of DMSO was set to 0.1% or less.

Cells generated by the following method were used as the iPS cell-derived hepatocytes (HiPS-HLCs) to be used in the co-culture of this Example. Human iPS cells were cultured for 4 days in a L-Wnt3A-expressing cell (ATCC, CRL2647) conditioned RPMI1640 medium (SIGMA) containing 100 ng/ml Activin A (R&D SYSTEMS), 4 mM L-Glutamine, 0.2% FBS (PAA LABORATORIES), and 1×B27 Supplement Minus Vitamin A (LIFE TECHNOLOGIES) to induce differentiation to definitive endoderm cells. For the induction of differentiation from the definitive endoderm cells to hepatoblasts, the cells were cultured for 5 days in a RPMI1640 medium containing 30 ng/ml BMP4 (R&D SYSTEMS), 20 ng/ml FGF4 (R&D SYSTEMS), 4 mM L-Glutamine, and 1×B27 Supplement Minus Vitamin A. For the induction of differentiation from the hepatoblasts to hepatocytes, the cells were cultured for 5 days in a RPMI1640 medium containing 20 ng/ml HGF, 4 mM L-Glutamine, and 1×B27 Supplement Minus Vitamin A, and then cultured for 11 days in Hepatocyte Culture Medium (HCM; LONZA) containing 20 ng/ml oncostatin M (OsM; R&D SYSTEMS) (the HCM medium used did not contain EGF) (WO 2014/168157 A1: PCT/JP2014/060228, JP 2016-10379 A: JP 2016-10379 A).

Figure 15A:
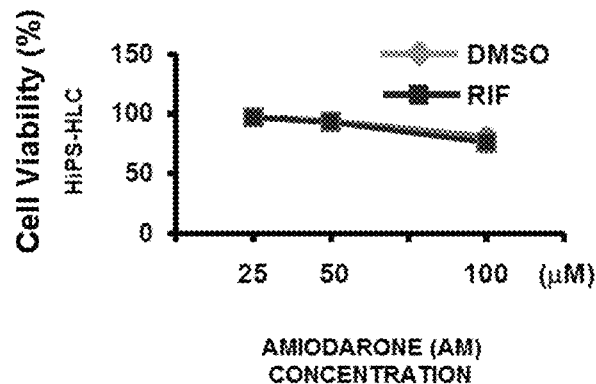
FIG. 15A, in which Caco-2 cells treated with RIF or a solvent (DMSO) were co-cultured with human iPS cell-derived hepatocytes (HiPS-HLCs), and simultaneously, the cells were subjected to the action of amiodarone (hereinafter referred to as "AM"), is a graph for showing results confirming that the presence or absence of RIF treatment on the Caco-2 cells does not change the cell viability in the HiPS-HLCs.
Figure 15B:
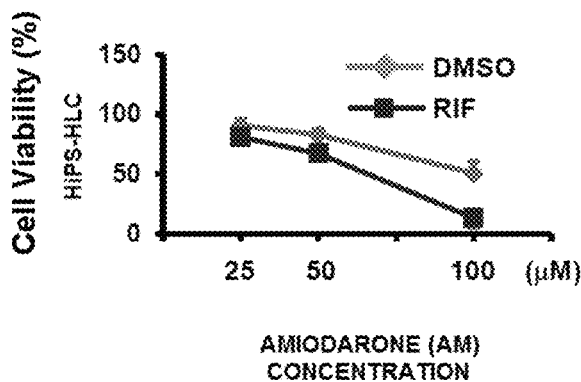
FIG. 15B, in which enterocyte-like cells (HiPS-ELC-TFs) treated with a solvent or RIF were co-cultured with HiPS-HLCs, and simultaneously, the cells were subjected to the action of AM, is a graph for showing results confirming that the RIF treatment on the HiPS-ELC-TFs cells lowers the cell viability in the HiPS-HLCs, and is a graph for showing results confirming an interaction between the CYP3A4 inducer (RIF) and the drug (AM) for the enterocyte-like cells (HiPS-ELC-TFs) (Example 11).

As a result, it was confirmed that, for the Caco-2 cells, there was no difference in HiPS-HLC cell viability between the RIF action group and the group with the action of only DMSO (FIG. 15A). It is predicted that, in the Caco-2 cells, CYP3A4 is not induced by RIF, and hence there is no difference in production amount of an AM metabolite showing hepatotoxicity (desethylamiodarone: hereinafter referred to as "DEA") between the RIF action group and the group with the action of only DMSO. Meanwhile, for the HiPS-ELC-TFs, the HiPS-HLC cell viability was significant lower in the RIF action group than in the DMSO action group (FIG. 15B). It was considered that, in the HiPS-ELC-TFs, CYP3A4 expression was activated by the action of RIF, and hence a larger amount of AM was metabolized to produce a larger amount of DEA showing hepatotoxicity, with the result that the cell viability of the HiPS-HLCs was lowered. It was considered that a system using the HiPS-ELC-TFs enabled in vitro evaluation of drug metabolism capacity by CYP3A4 induced by a drug.

Example 12

Confirmation of Drug Metabolism Capacity in Enterocyte-Like Cells

In this Example, with regard to the enterocyte-like cells (HiPS-ELC-TFs) of the present invention, a CYP3A4 inhibitor and its influence on drug metabolism were confirmed. When a drug is taken, for example, a component contained in food may cause a change in pharmacokinetics of the drug. In view of this, in this Example, an influence on the drug metabolism of AM in a system containing coumarins (6',7'-dihydroxybergamottin and bergamottin), each serving as a component of GFJ known to inhibit CYP3A4 activity, was confirmed.

Figure 16:
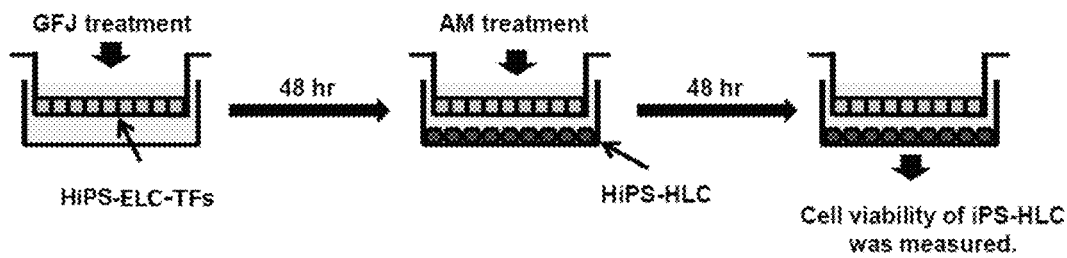
FIG. 16 is a diagram for illustrating an experimental method for the confirmation of the influence of a CYP3A4 inhibitor on drug metabolism in enterocyte-like cells (HiPS-ELC-TFs) (Example 12).

In the same manner as in Example 11, the HiPS-ELC-TFs were generated by the same procedure as in Example 7, and Caco-2 cells were used as control cells. The HiPS-ELC-TFs or the Caco-2 cells were subjected to the actions of the coumarins (6',7'-dihydroxybergamottin and bergamottin) (10 µM and 2 µM, respectively), each serving as a component of GFJ, for 48 hours, and then AM (50 µM, 100 µM, or 200 µM), which was to be metabolized by CYP3A4 to cause hepatotoxicity, was added to the medium. Simultaneously with the addition of AM, co-culture of the HiPS-ELC-TFs and human iPS cell-derived hepatocytes (HiPS-HLCs) was initiated, and the influence on the cell viability was confirmed (FIG. 16). In the drawings, the coumarins (6',7'-dihydroxybergamottin and bergamottin) are represented as "GFJ".

Figure 17A:
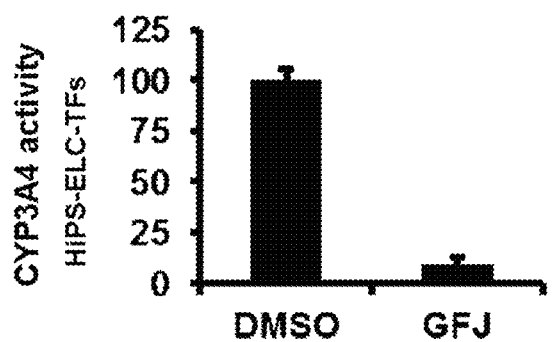
FIG. 17A is a graph for confirming that the CYP3A4 activity of enterocyte-like cells (HiPS-ELC-TFs) is suppressed by a component of grapefruit juice (hereinafter referred to as "GFJ") serving as a CYP3A4 inhibitor.
Figure 17B:
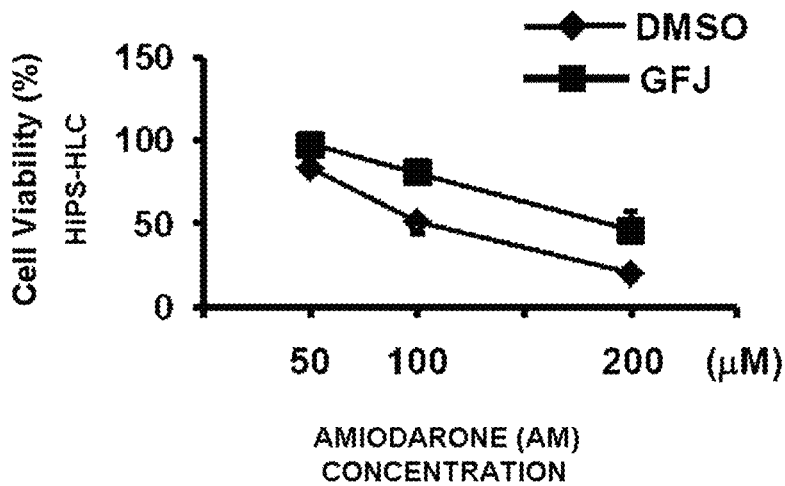
FIG. 17B, in which enterocyte-like cells (HiPS-ELC-TFs) treated with a solvent or GFJ were co-cultured with HiPS-HLCs, and simultaneously, the cells were subjected to the action of AM, is a graph for showing results confirming that the GFJ treatment on the HiPS-ELC-TFs cells improves the cell viability in the HiPS-HLCs.

As a result, the CYP3A4 activity of the HiPS-ELC-TFs in the GFJ action group was suppressed to 10 or less with respect to the value in the DMSO action group defined as 100 (FIG. 17A). Meanwhile, the cell viability of the HiPS-HLCs in the system in which AM (100 µM or 200 µM) was added to the medium showed a higher value in the GFJ action group than in the DMSO action group (FIG. 17B). From this, it was considered that the CYP3A4 activity of the HiPS-ELC-TFs was suppressed by GFJ, and the resultant suppression of the drug metabolism of AM suppressed the production of DEA, resulting in the suppression of the influence on cytotoxicity. It was considered that a system using the HiPS-ELC-TFs enabled in vitro evaluation of changes in levels of the drug efficacy and toxicity of a drug used in combination due to the inhibition of CYP3A4 by a component contained in food.

In order to measure CYP3A4 activity in the HiPS-ELC-TFs, P450-Glo™ 3A4 (catalog number; V9001) Assay Kit (PROMEGA) was used. The activity was measured using a luminometer (LUMAT LB 9507; BERTHOLD). Each CYP3A4 activity value was corrected with the total protein amount per well.

Example 13

Confirmation of Tight Junctions of Enterocyte-Like Cells

Figure 18A:
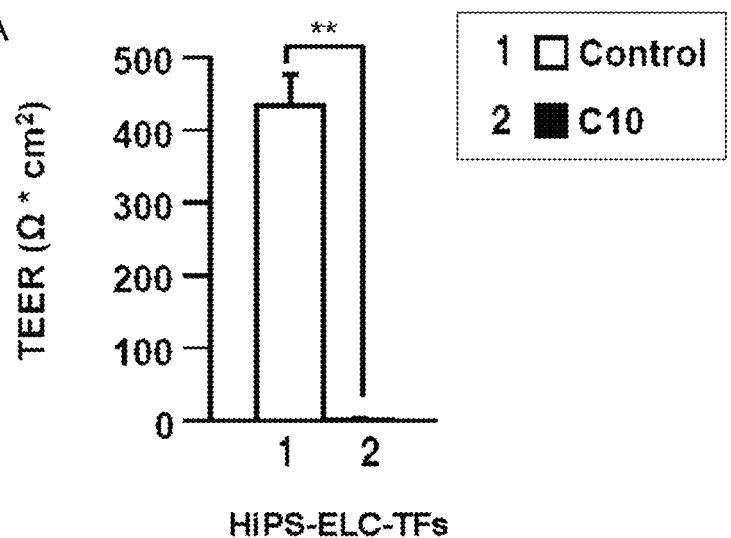
FIGS. 18A and 18B are graphs for showing results confirming the tight junction function of enterocyte-like cells.
Figure 18B:
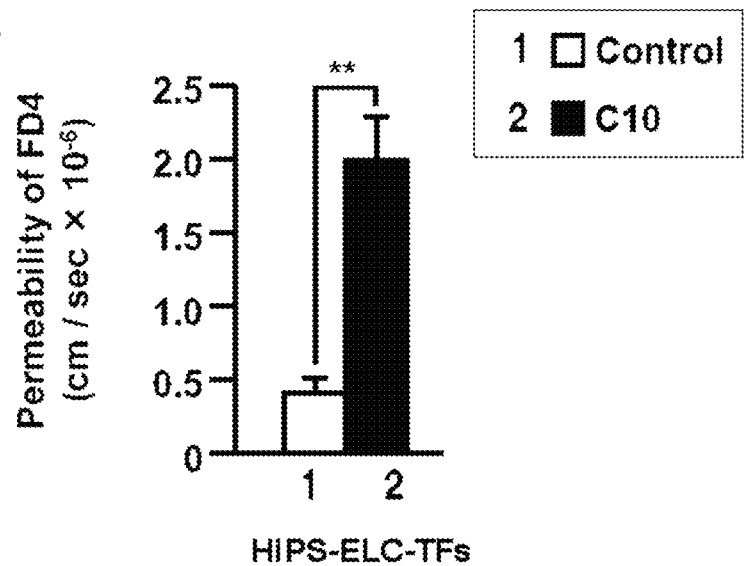

In this Example, the tight junction function of the enterocyte-like cells (HiPS-ELC-TFs) of the present invention was confirmed. It is known that enterocytes strongly join together to form tight junctions. The tight junction function was confirmed by measuring TEER by the same procedure as in Example 6. In addition, an FD4 (fluorescein isothiocyanate-dextran: average molecular weight 4,000) permeation test was also performed. The TEER of the enterocyte-like cells (HiPS-ELC-TFs) was about 430 $\Omega \cdot cm^2$ (FIG. 18A). When capric acid (C10) serving as a tight junction opener was allowed to act, the TEER value of the HiPS-ELC-TFs became substantially 0 $\Omega \cdot cm^2$ (FIG. 18A). In addition, the Papp (permeability coefficient) of FD4 was about $0.4 \times 10^{-6}$ (cm/sec) (FIG. 18B). The Papp value of FD4 was greatly increased by the action of C10 (FIG. 18B). The above-mentioned results suggested that the HiPS-ELC-TFs had a tight junction function and had a barrier function.

The Papp value was calculated using the following equation.

$Papp = \delta Cr/\delta t \times Vr/(A \times C0)$

δCr=final receiver concentration; δt=assay time; Vr=receiver volume A=transwell growth area; C0=FD4 concentration in the donor compartment Example 14

Confirmation of Tight Junctions of Enterocyte-Like Cells

Figure 19:
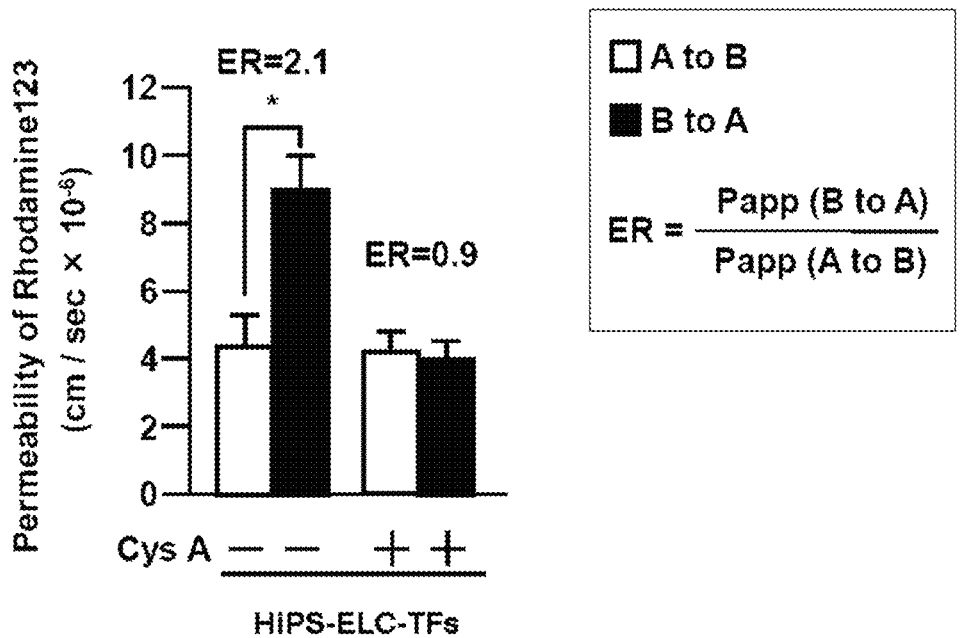
FIG. 19 is a graph for showing results confirming the P-gp function of enterocyte-like cells (HiPS-ELC-TFs) (Example 14).

P-gp is a member of the ABC transporter family, which exports a foreign substance, a drug, and the like to the outside of cells in gastrointestinal mucosa, renal tubular epithelial cells, cerebrovascular endothelial cells (blood-brain barrier), and the like. P-gp influences the bioavailability of a drug and the distribution of a drug to a target tissue. In this Example, in order to evaluate the function of P-gp in the enterocyte-like cells (HiPS-ELC-TFs) of the present invention, a drug permeation test using Rhodamine 123 (action concentration: 10 µM) was performed. It is known that Rhodamine 123 is a substrate for P-gp. P-gp is a transporter expressed on an apical side, and hence, when P-gp is functioning, the accumulation of Rhodamine 123 on the apical side can be confirmed. It was actually found that the permeability coefficient of Rhodamine 123 to a basolateral side (A to B) in the HiPS-ELC-TFs was significantly smaller than the permeability coefficient to the apical side (B to A) (ER value: 2.1). Therefore, it was suggested that P-gp was functioning in the HiPS-ELC-TFs. Further, when P-gp was inhibited with cyclosporin A (CysA, action concentration: 10 µM), significant B-to-A permeation of Rhodamine 123 became unable to be confirmed (ER value: 0.9). The results suggested that the B-to-A transport of Rhodamine 123, which had been confirmed in the HiPS-ELC-TFs, was mediated by P-gp (FIG. 19).

Example 15

Method for Inducing Differentiation to Enterocyte-Like Cells Using MATRIGEL

Figure 20:
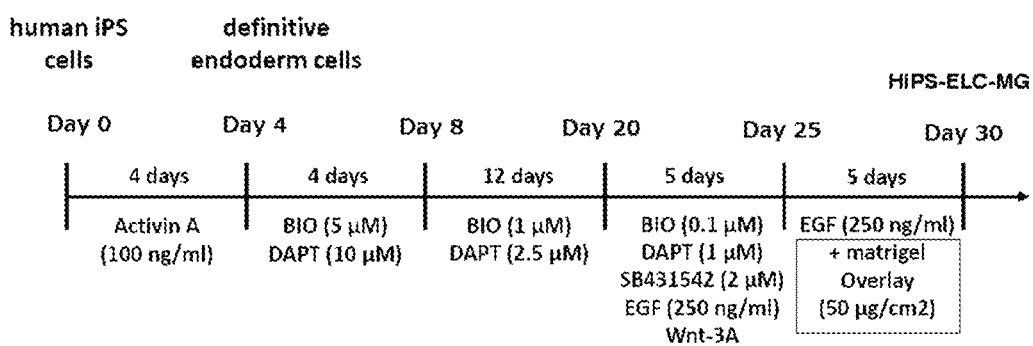
FIG. 20 is a diagram for illustrating a method for inducing differentiation to enterocyte-like cells (HiPS-ELC-MGs) using MATRIGEL (Example 15).

In this Example, a method for inducing differentiation to enterocyte-like cells in a system overlaid with MATRIGEL is described. In this Example, Tic (JCRB1331) was used as a human iPS cell line, and cultured by the method described in Example 1 using the medium 1. Differentiation induction treatment was performed by adding 100 ng/ml Activin A to the culture system of the human iPS cell line (Tic) and culturing the cells for 4 days. Thus, definitive endoderm cells were generated. The generated definitive endoderm cells were further cultured using the medium 3. During a period from day 4 to day 8 after the initiation of differentiation induction, BIO (5 µM) and DAPT (10 µM) were added to the culture system, and then BIO (1 µM) and DAPT (2.5 µM) were added to the culture system. Further, thereafter until day 25, the cells were further cultured for 5 days using the medium 3 supplemented with BIO (0.1 µM), DAPT (1 µM), SB431542 (2 µM), EGF (250 ng/mL), and Wnt3a. After that, with the use of the medium 3 containing EGF (250 ng/ml), after overlaying of 50 µg/cm$^2$ MATRIGEL, the cells were cultured for 5 days (FIG. 20). In the following Examples, the enterocyte-like cells generated in this Example without MATRIGEL-overlaying treatment are referred to as HiPS-ELC-Cs, and the enterocyte-like cells generated in the system containing MATRIGEL are referred to as HiPS-ELC-MGs.

Experimental Example 15-1

Investigation of Efficiency of Differentiation to Enterocyte-Like Cells

For the enterocyte-like cells (HiPS-ELC-Cs and HiPS-ELC-MGs) generated in Example 15 above and various cells, analysis of small intestine-related gene expression was performed. The expressions of genes were analyzed for iPSCs (undifferentiated human iPS cells), the HiPS-ELC-Cs, the HiPS-ELC-MGs, LS180 cells (human colon adenocarcinoma-derived cells), Caco-2 cells (human colon carcinoma-derived cells), and AI. The expressions of the genes were each measured by a quantitative real-time RT-PCR method using SYBR Green gene expression assays (APPLIED BIOSYSTEMS).

The results of the foregoing confirmed that the gene expression level of each of VILLIN, SI, Intestine Specific Homeohox, and CDX2 in the HiPS-ELC-MGs was significantly higher than that in the HiPS-ELC-Cs (FIG. 21).

Experimental Example 15-2

Investigation of Efficiency of Differentiation to Enterocyte-Like Cells

Figure 22:
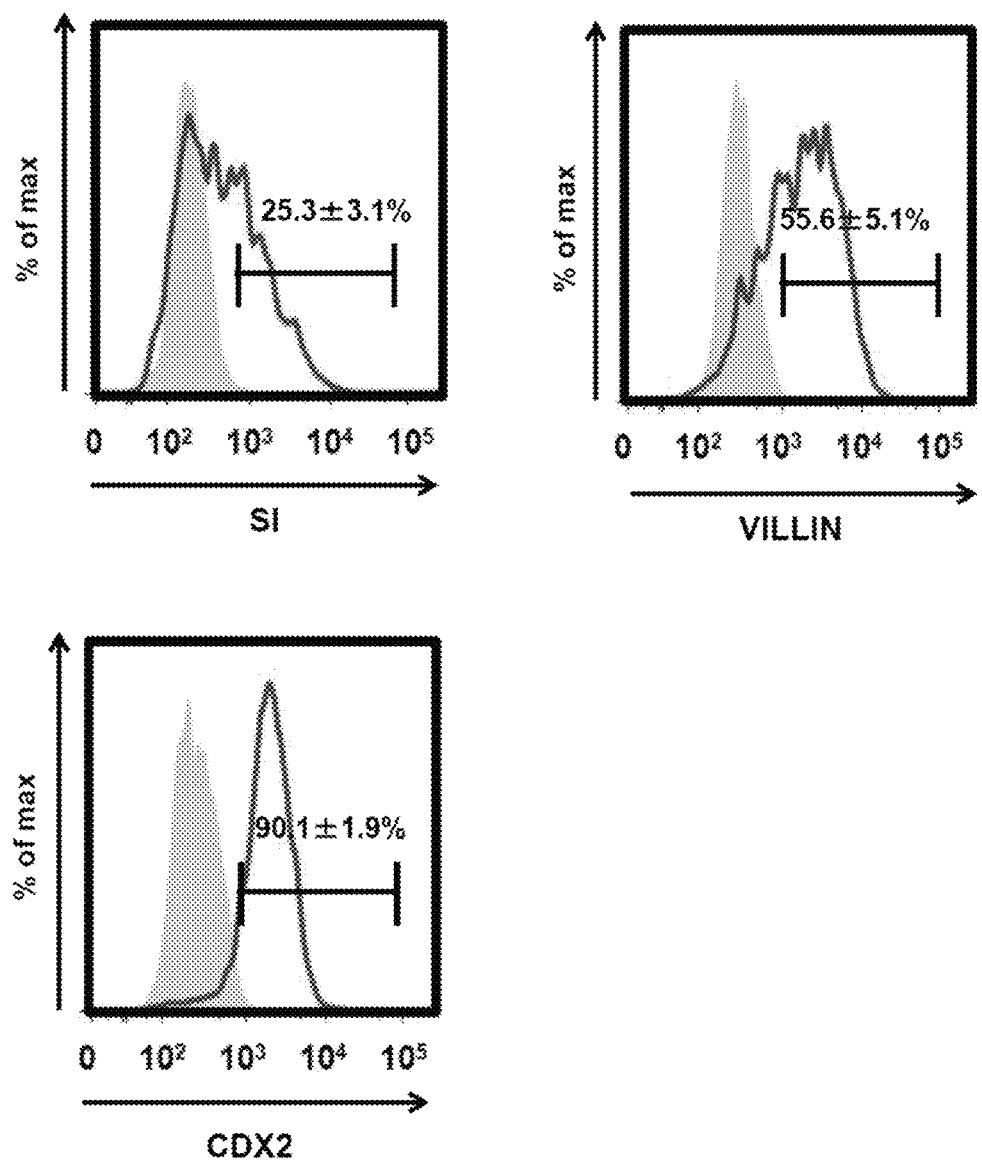
FIG. 22 are graphs for showing results of FACS analysis for the gene expression of each of small intestine-related genes SI, VILLIN, and CDX2 for enterocyte-like cells (HiPS-ELC-MGs) (Experimental Example 15-2).

For the HiPS-ELC-MGs generated in Example 15 above, the gene expression ratio of each of small intestine-related genes SI, VILLIN, and CDX2 was measured by FACS analysis. The results were as follows: 25.3%, 55.6%, and 90.1% of the HiPS-ELC-MGs were SI-positive cells, VILLIN-positive cells, and CDX2-positive cells, respectively. Thus, it was confirmed that the HiPS-ELC-MGs were enterocyte-like cells (FIG. 22).

Experimental Example 15-3

Confirmation of CYP Induction Potency of Enterocyte-Like Cells

Figure 23:
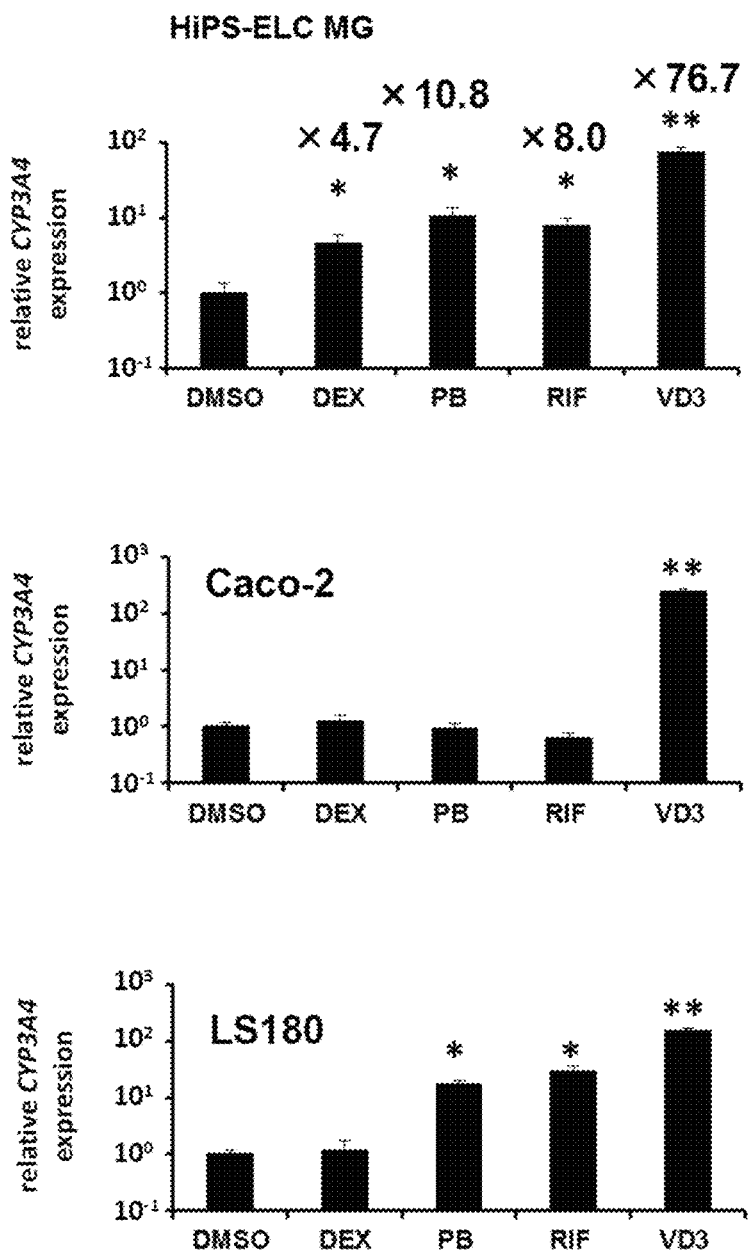
FIG. 23 are graphs for showing results of evaluation of CYP3A4 induction potency for enterocyte-like cells (HiPS-ELC-MGs) and various cells (Experimental Example 15-3).

For the HiPS-ELC-MGs generated in Example 15 above, a CYP3A4 expression level was measured, and CYP3A4 induction potency for various CYP3A4 inducers was evaluated. The CYP3A4 expression level was measured by the same procedure as in Example 10. As the CYP3A4 inducers, dexamethasone (DEX), phenobarbital (PB), RIF, and VD3 were used. As comparative cells, Caco-2 cells and LS180 cells were similarly investigated. In the HiPS-ELC-MGs, in the case of using any of the CYP3A4 inducers, significant expression induction of CYP3A4 was confirmed. Meanwhile, in the Caco-2 cells, CYP3A4 induction was confirmed only in the case of using VD3, and in the LS180 cells, CYP3A4 induction by DEX was not confirmed. From the foregoing, it was suggested that the human iPS cell-derived enterocyte-like cells were a more suited model for the evaluation of CYP3A4 induction than the Caco-2 cells or the LS180 cells (FIG. 23).

Experimental Example 15-4

Figure 24:
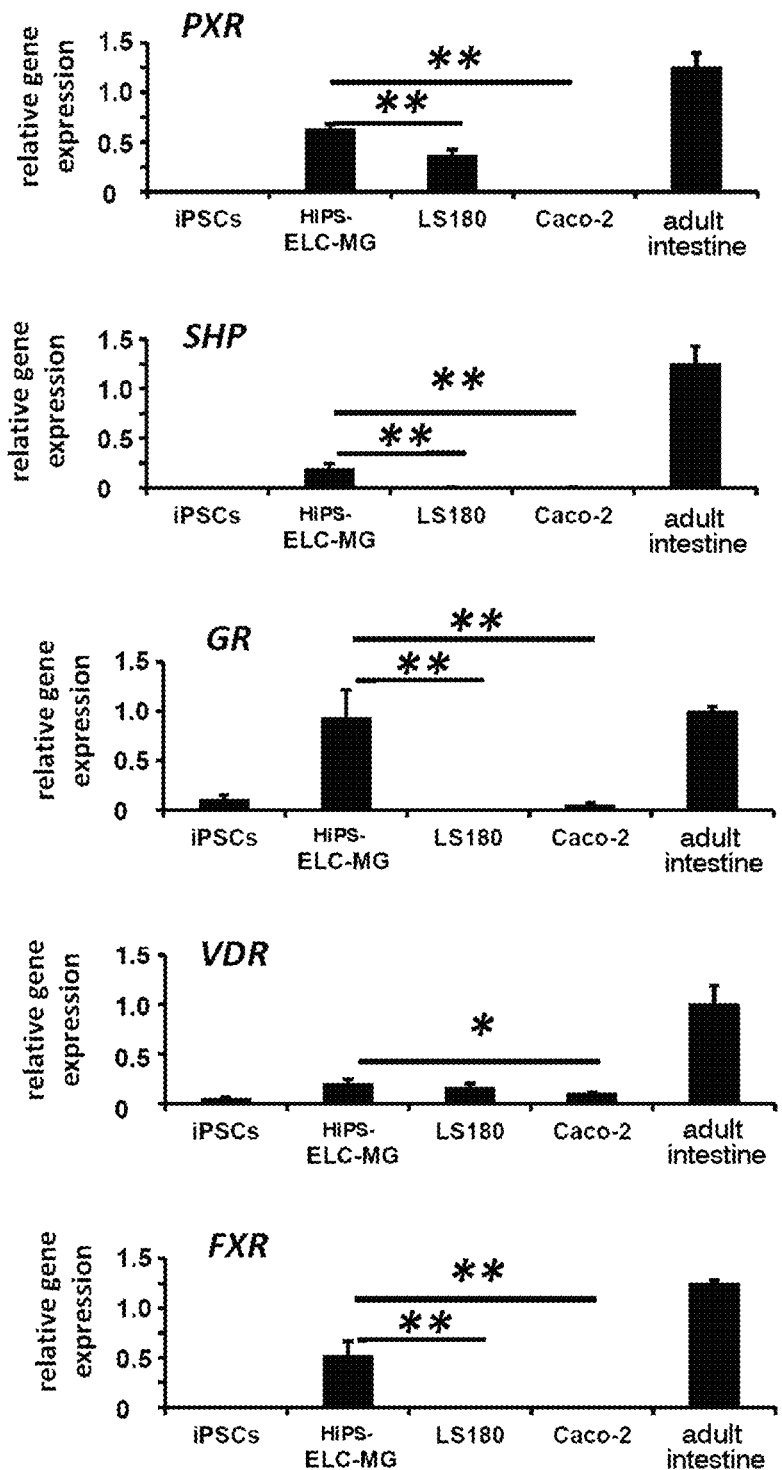
FIG. 24 are graphs for showing results of expression analysis of small intestinal nuclear receptor genes (PXR, SHP, GR, VDR, and FXR) for enterocyte-like cells (HiPS-ELC-MGs) and various cells (Experimental Example 15-4).

Gene Expression Analysis of Small Intestinal Nuclear Receptor of Enterocyte-Like Cells It is known that a nuclear receptor plays an important role in CYP3A4 induction. For the enterocyte-like cells (HiPS-ELC-MGs) generated in Example 15 above and various cells, gene expression analysis of small intestinal nuclear receptors was performed. Confirmation was made for pregnane X receptor (PXR) essential for CYP3A4 expression induction by phenobarbital (PB) or RIF, glucocorticoid receptor (GR) essential for CYP3A4 expression induction by DEX, and vitamin D receptor (VDR) essential for CYP3A4 expression induction by VD3, which served as the small intestinal nuclear receptors. The expressions of the genes were analyzed for iPSCs (undifferentiated human iPS cells), the HiPS-ELCs, LS180 cells, Caco-2 cells, and AI. The expressions of the genes were each measured by a quantitative real-time RT-PCR method using SYBR Green gene expression assays (APPLIED BIOSYSTEMS). The results of the foregoing found that PXR was expressed in each of the HiPS-ELC-MGs and the LS180 cells at a level about half that in the Small Intestine. GR was strongly expressed only in the HiPS-ELC-MGs. It was able to be confirmed that VDR was expressed in each of the HiPS-ELC-MGs, the LS180 cells, and the Caco-2 cells, though weakly (FIG. 24). This suggests that the HiPS-ELC-MGs have an expression pattern of nuclear receptors closer to that of the AI tissue than the LS180 cells or the Caco-2 cells.

INDUSTRIAL APPLICABILITY

As described in detail above, the cells obtained by the method for inducing differentiation of the present invention express markers expressed by enterocytes, express a drug-metabolizing enzyme and transporters, and have a tight junction function, and hence can be said to be "enterocyte-like cells." In particular, the expression levels of the drug-metabolizing enzyme and the transporters are excellent as compared to those in hitherto generally used Caco-2 cells. As a result of the foregoing, it has become possible to efficiently generate enterocyte-like cells that enable simultaneous evaluation of drug metabolism and drug absorption. Further, human primary enterocytes have been difficult to acquire, and have had a problem of differences in properties due to individual differences. However, the method for inducing differentiation of the present invention has enabled stable provision of excellent enterocyte-like cells. Accordingly, the present invention enables stable testing for drug metabolism and permeability in the small intestine, is expected to be able to greatly contribute to, for example, drug development of pharmaceuticals and the like, and analysis and development of food and the like, and hence is useful.

The invention claimed is:

1. A method for inducing differentiation from pluripotent stem cells to enterocyte-like cells, the method comprising the steps of:
   1) inducing differentiation from pluripotent stem cells to definitive endoderm cells; and
   2) culturing the definitive endoderm cells obtained by the inducing differentiation in a system containing comprising
      a) 0.02 μM to 20 μM of an ALK5 inhibitor,
      b) 0.1 nM to 10 mM of Wnt3a,
      c) 10 ng/mL to 1,000 ng/mL of epidermal growth factor (EGF),
      d) 0.01 μM to 10 μM of 6-bromoindirubin-3'-oxime (BIO), which is GSK-3 Inhibitor IX, and
      e) 0.02 μM to 20 μM of N-[(3,5-difluorophenyl)acetyl]-L-alanyl-2-phenyl]glycine-1,1-dimethylethyl ester (DAPT), which is a γ-secretase inhibitor.

2. A method for inducing differentiation from pluripotent stem cells to enterocyte-like cells according to claim 1, further comprising a step of introducing CDX2 gene during any one of the step 1) or the step 2).

3. A method for inducing differentiation from pluripotent stem cells to enterocyte-like cells according to claim 1, further comprising a step of introducing FOXA2 gene during any one of the step 1) or the step 2).

4. A method for inducing differentiation according to claim 1, further comprising, after the step of culturing the definitive endoderm cells in the step 2), a treatment step of overlaying a basement membrane matrix on the cultured cells.

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Artificial
<220> FEATURE:
<223> OTHER INFORMATION: a K7 peptide tag

<400> SEQUENCE: 1

Lys Lys Lys Lys Lys Lys Lys
1               5